(12) United States Patent
Kraft

(10) Patent No.: US 12,251,685 B2
(45) Date of Patent: Mar. 18, 2025

(54) CATALYTICALLY ACTIVE SUBSTANCES

(71) Applicant: ILLUMINA, INC., San Diego, CA (US)

(72) Inventor: Lewis J. Kraft, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 496 days.

(21) Appl. No.: 17/359,198

(22) Filed: Jun. 25, 2021

(65) Prior Publication Data

US 2021/0322962 A1    Oct. 21, 2021

Related U.S. Application Data

(62) Division of application No. 16/626,312, filed as application No. PCT/US2018/064445 on Dec. 7, 2018, now abandoned.

(60) Provisional application No. 62/609,370, filed on Dec. 22, 2017.

(51) Int. Cl.
| | |
|---|---|
| *B01J 31/22* | (2006.01) |
| *B01J 27/043* | (2006.01) |
| *B01J 37/02* | (2006.01) |
| *C07D 249/04* | (2006.01) |
| *C08F 220/56* | (2006.01) |
| *C12Q 1/6874* | (2018.01) |

(52) U.S. Cl.
CPC ......... *B01J 27/043* (2013.01); *B01J 31/2286* (2013.01); *B01J 37/0219* (2013.01); *C07D 249/04* (2013.01); *C08F 220/56* (2013.01); *C12Q 1/6874* (2013.01); *B01J 2219/00621* (2013.01); *B01J 2219/00626* (2013.01); *B01J 2219/00635* (2013.01); *B01J 2219/00637* (2013.01); *B01J 2219/00722* (2013.01); *B01J 2231/321* (2013.01); *B01J 2531/16* (2013.01)

(58) Field of Classification Search
CPC ............... B01J 37/0219; B01J 31/2286; B01J 37/0209; B01J 35/023; B01J 27/043; B01J 2219/00635; B01J 2219/00637; B01J 2219/00621; B01J 2219/00626; B01J 2219/00722; B01J 2231/321; B01J 2531/16; C08F 220/54; C08F 220/56; C08F 220/603; C12Q 1/6874; C07D 249/04
See application file for complete search history.

(56) References Cited

U.S. PATENT DOCUMENTS

| | | | |
|---|---|---|---|
| D825,078 S | 8/2018 | Osmus et al. | |
| 2002/0137096 A1 | 9/2002 | Fodor et al. | |
| 2004/0171053 A1 | 9/2004 | Hu | |
| 2010/0121022 A1 | 5/2010 | Musa et al. | |
| 2012/0010395 A1 | 1/2012 | Skrzypczynski et al. | |
| 2014/0079923 A1 | 3/2014 | George et al. | |
| 2015/0005447 A1 | 1/2015 | Berti et al. | |
| 2018/0327832 A1 | 11/2018 | Ramirez et al. | |

FOREIGN PATENT DOCUMENTS

| | | | |
|---|---|---|---|
| CL | 200202666 | 11/2002 | |
| CN | 103059006 A | 4/2013 | |
| CN | 103435448 A | 12/2013 | |
| CN | 104968427 A | 10/2015 | |
| CN | 105431554 A | 3/2016 | |
| JP | 2015529576 A | 10/2015 | |
| RU | 2060993 C1 | 5/1996 | |
| WO | 2006012569 A1 | 2/2006 | |
| WO | WO-2013184796 A1 * | 12/2013 | ............... B05D 3/06 |
| WO | 2015095291 A1 | 6/2015 | |

OTHER PUBLICATIONS

Vutti et al. Covalent and Stable CuAAC Modification of Silicon Surfaces for Control of Cell Adhesion. ChemBioChem 2015, 16, 782-791 (Year: 2015).*
Stanislav et al. Analysis and Optimization of Copper-Catalyzed Azide-Alkyne Cycloaddition for Bioconjugation. Angew Chem Int Ed Engl. 2009 ; 48(52): 9879-9883. (Year: 2009).*
Droumaguet, et al., "Click chemistry: a powerful tool to create polymer-based macromolecular chimeras",Macromolecular Rapid Commun., vol. 29, pp. 1073-1089, 2008.
Liang, L., et al., "The Copper(I)-Catalyzed Alkyne-Azide Cycloaddition (CuAAC) "click" Reaction and Its Applications, an Overview",Coordination Chemistry Reviews, vol. 255, pp. 2933-2945, Jul. 6, 2011.
Marks, et al., "Strain-promoted "click" chemistry for terminal labeling of DNA",Bioconjugate Chem., vol. 22, pp. 1259-1263, 2011.
Witt, et al., "Selective Growth of Gold onto Copper Indium Sulfide Selenide Nanoparticles",Z. Naturforsch., 68a, pp. 398-404, 2013.
Gawandi, et al., "Cu and Cu-Based Nanoparticles: Synthesis and Applications in Catalysis",Chem. Rev., 116, pp. 3722-3811, 2016.
Nandi, D. et al., "Light effect on Click reaction: Role of photonic quantum dot catalyst",Scientific Reports, 6:33025, 10 pages, Sep. 13, 2016.
Ramirez, et al., CL-201700934-S, Industrial Design, Granted, Chile, Assignee, Illumina, Inc.,Des. 825,078S cited above is corresp. Eng. Lang Des. Patent, Nov. 17, 2017.

(Continued)

*Primary Examiner* — Shafiqul Haq
(74) *Attorney, Agent, or Firm* — Dierker & Kavanaugh, P.C.

(57) ABSTRACT

A catalytically active substance includes a copper (I) sulfide mineral particle, and an alkyne functionalized molecule bound to a surface of the copper (I) sulfide mineral particle. In an example method, a copper (I) sulfide mineral is reacted with an alkyne functionalized molecule to form a catalytically active substance. The catalytically active substance is reacted with an azide functionalized molecule to couple the catalytically active substance with the azide functionalized molecule.

22 Claims, 4 Drawing Sheets

(56) References Cited

OTHER PUBLICATIONS

Yang, D., et al., "Poly(thymine)-Templated Selective Formation of Copper Nanoparticles for Alakaline Phosphatase Analysis Aided by Alkyne-Azide Cycloaddition "Click" Reaction",Applied Nano Materials, vol. 1, pp. 1-34, (online), Dec. 12, 2017.
Zou, et al., "Nonstoichiometric copper chalcogenides for photo-activated alkyne/azide cycloaddition",Phys. Chem. Chem. Phys., 19, pp. 6964-6968, Feb. 22, 2017.
ISA, "International Search Report and Written Opinion for International Application No. PCT/US2018/064445",12 pages, Apr. 24, 2019.
Ramirez, et al., CL-201903184-A1 Invention Patent Application, Chile, Assignee Illumina, Inc., US20180327832A1 cited above is corresp. Eng. Lang. app., May 22, 2020.
Himo, et al., "Copper(I)-Catalyzed Synthesis of Azoles. DFT Study Predicts Unprecedented Reactivity and Intermediates", J. Am. Chem. Soc. 127, 2005, pp. 210-216, 2005.
Rozkiewicz, et al., "Transfer Printing of DNA by "Click" Chemistry", ChemBioChem, 2007, 1997-2002, 2007.
Gutmann, et al., "Biocompatible azide-alkyne "click" reactions for surface decoration of glyco-engineered cells", ChemBioChem 17(9), 2016, pp. 866-875, Mar. 21, 2016.
Saini, et al., "Robust and Versatile Cu(I) metal frameworks as potential catalysts for azide-alkyne cycloaddition reactions: Review", Molecular Catalysis vol. 504, Article 111424, Mar. 2021.
Devaraj et al., "Chemoselective Covalent Coupling of Oligonucleotide Probes to Self-Assembled Monolayers", Journal of the American Chemical Society, 127(24), 8600-8601. doi:10.1021/ja0514621, May 28, 2005.

\* cited by examiner

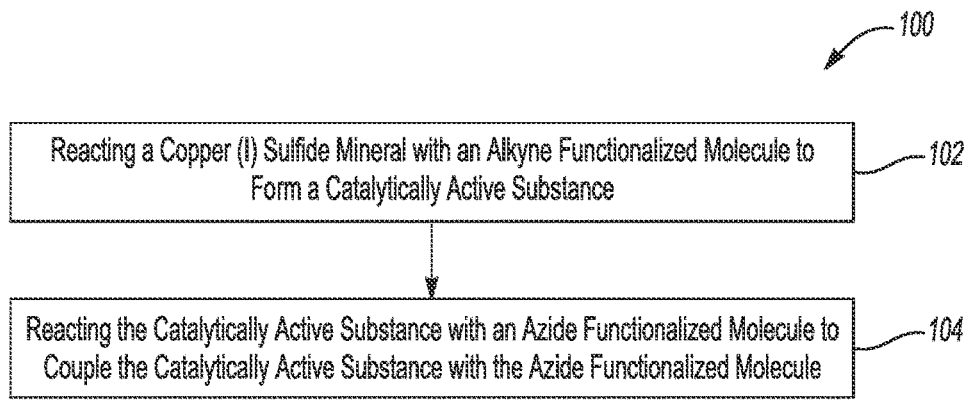
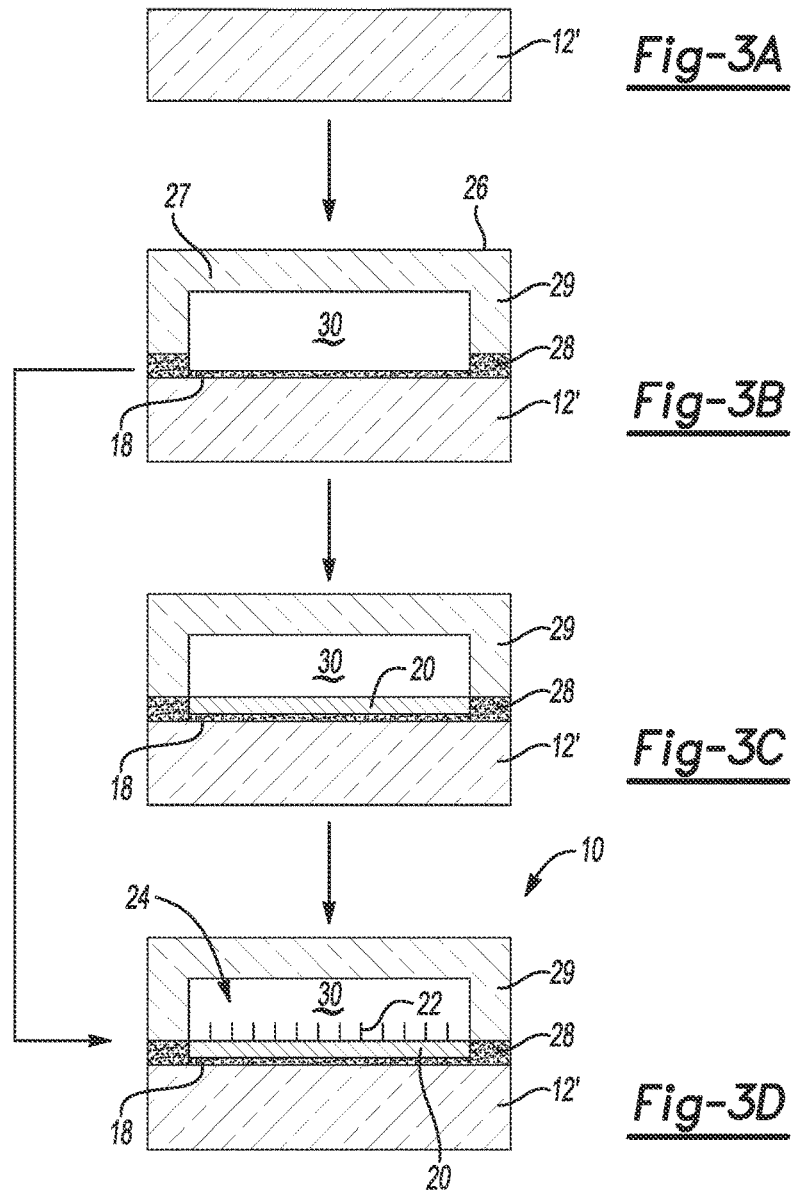

CATALYTICALLY ACTIVE SUBSTANCES

CROSS-REFERENCE TO RELATED APPLICATIONS

This application is a divisional of U.S. Ser. No. 16/626,312, filed Dec. 23, 2019, which is itself a national stage entry under 35 U.S.C. § 371 of PCT/US2018/064445, filed Dec. 7, 2018, which itself claims the benefit of U.S. Provisional Application Ser. No. 62/609,370, filed Dec. 22, 2017, the content of each of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes of humans and other organisms. In certain applications, for example, individual DNA and RNA probes may be attached at locations in a geometric grid (or randomly) on an array support. A test sample, e.g., from a person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

INTRODUCTION

In an aspect, a catalytically active substance comprises a copper (I) sulfide mineral particle; and an alkyne functionalized molecule directly bound to a surface of the copper (I) sulfide mineral particle.

In an example of this aspect, the copper (I) sulfide mineral particle is selected from the group consisting of chalcocite, djurleite, and digenite.

In an example of this aspect, the alkyne functionalized molecule is a primer having an alkyne functional group, optionally wherein the alkyne functional group is attached at the 5' terminus of the primer.

In an example of this aspect, a coordinate bond binds the alkyne functionalized molecule to the surface of the copper (I) sulfide mineral particle.

It is to be understood that any features of this aspect of the catalytically active substance may be combined together in any desirable manner and/or configuration.

In another aspect, a method comprises reacting a copper (I) sulfide mineral with an alkyne functionalized molecule to form a catalytically active substance; and reacting the catalytically active substance with an azide functionalized molecule to couple the catalytically active substance with the azide functionalized molecule. In another aspect, a method of making a triazole comprises reacting an alkyne functionalized molecule with an azide functionalized molecule in the presence of a copper (I) sulfide mineral.

In an example of this aspect, the method further comprises filtering unreacted copper (I) sulfide mineral from the catalytically active substance prior to reacting the catalytically active substance with the azide functionalized molecule.

In an example of this aspect, prior to reacting the copper (I) sulfide mineral with the alkyne functionalized molecule, the method further comprises adding a stoichiometric excess of the copper (I) sulfide mineral, with respect to the alkyne functionalized molecule, to the alkyne functionalized molecule.

In an example of this aspect, the copper (I) sulfide has an average particle size ranging from about 500 nm to about 45 μm.

In an example of this aspect, reacting the copper (I) sulfide mineral with the alkyne functionalized molecule involves forming a mixture of the copper (I) sulfide mineral, the alkyne functionalized molecule, and a solvent of the alkyne functionalized molecule; and maintaining the mixture at a temperature that is above a freezing point of the solvent and below a boiling point of the solvent for a time up to about 50 days. In this example, the solvent is selected from the group consisting of water, a sodium carbonate buffer, a potassium phosphate buffer, and dimethyl sulfoxide; and a pH of the mixture ranges from about 4 to about 12. Also in this example, the maintaining involves heating the mixture to a temperature ranging from about 30° C. to about 60° C. for a time ranging from about 30 minutes to about 90 minutes.

In an example of this aspect, prior to reacting the alkyne functionalized molecule or the catalytically active substance with the azide functionalized molecule, the method further comprises forming a layer of the azide functionalized molecule on a surface of a flow cell substrate, and wherein the alkyne functionalized molecule or the catalytically active substance is reacted with the layer of the azide functionalized molecule on the surface of the flow cell substrate. In this example, the alkyne functionalized molecule or the catalytically active substance is present in a liquid mixture, and wherein the liquid mixture is flowed over the layer of the azide functionalized molecule on the surface of the flow cell substrate. Also in this example, prior to forming the layer, the method may further comprise attaching a silane or a silane derivative to the surface of the substrate to form a silanized surface.

In an example of this aspect, the method is performed without ligand coordination and without exposure to a reducing agent.

It is to be understood that any features of this aspect of the method may be combined together in any desirable manner. Moreover, it is to be understood that any combination of features of this aspect of the method and/or of the aspect of the catalytically active substance may be used together, and/or that any features from either or both of these aspects may be combined with any of the examples disclosed herein.

In still another aspect, a graft mix, comprises a primer including an alkyne functional group; a solvent; and a copper (I) sulfide mineral.

In an example of this aspect, the alkyne functional group is to react with a surface of the copper (I) sulfide mineral to form a catalytically active substance in the graft mix.

In an example of this aspect, the graft mix further comprises an azide functionalized molecule, wherein the azide functionalized molecule is to react with the alkyne functionalized molecule, mediated by the copper (I) sulfide mineral. In an example, the azide functionalized molecule is a polymer. In an example, the polymer is on a surface of a substrate, optionally wherein the substrate is a flow cell.

In an example of this aspect, the graft mix includes a stoichiometric excess of the copper (I) sulfide mineral with respect to the primer.

In an example of this aspect, the graft mix includes from about 1 µM to about 20 µM of the primer; and from about 0.1 M to about 3 M of the copper (I) sulfide mineral.

In an example of this aspect, the copper (I) sulfide mineral is selected from the group consisting of chalcocite, djurleite, and digenite, and has an average particle size ranging from about 500 nm to about 45 µm.

It is to be understood that any features of this aspect of the graft mix may be combined together in any desirable manner. Moreover, it is to be understood that any combination of features from either the graft mix and/or from the method and/or from the catalytically active substance may be used together, and/or that any features from any or all of these aspects may be combined with any of the features of the examples disclosed herein.

In yet a further aspect, a method of grafting a primer to a flow cell surface comprises reacting an alkyne functionalized primer in the presence of a copper (I) sulfide mineral with an azide functionalized molecule on the flow cell surface.

In an example of this further aspect, the copper (I) sulfide mineral reacts with the alkyne functionalized primer to form a catalytically active substance, and the catalytically active substance reacts with the azide functionalized molecule to couple the catalytically active substance with the azide functionalized molecule on the flow cell surface. In some examples, prior to reacting the copper (I) sulfide mineral with the alkyne functionalized primer, the method further comprises adding a stoichiometric excess of the copper (I) sulfide mineral, with respect to the alkyne functionalized primer, to the alkyne functionalized primer. In some examples, the reacting of the copper (I) sulfide mineral with the alkyne functionalized primer involves forming a mixture of the copper (I) sulfide mineral, the alkyne functionalized primer, and a solvent of the alkyne functionalized primer, and maintaining the mixture at a temperature that is above a freezing point of the solvent and below a boiling point of the solvent for a time up to about 50 days. In some of these examples, the solvent is selected from the group consisting of water, a sodium carbonate buffer, a potassium phosphate buffer, and dimethyl sulfoxide, and a pH of the mixture ranges from about 4 to about 12. Also in some of these examples, the maintaining involves heating the mixture to a temperature ranging from about 30° C. to about 60° C. for a time ranging from about 30 minutes to about 90 minutes.

In an example of this further aspect, prior to reacting the catalytically active substance with the azide functionalized molecule on the flow cell surface, the method further comprises forming a layer of the azide functionalized molecule on the flow cell surface, and wherein the catalytically active substance is reacted with the layer of the azide functionalized molecule on the flow cell surface. In this example, the catalytically active substance is present in a liquid mixture, and the liquid mixture is flowed over the layer of the azide functionalized molecule on the flow cell surface. In some of these examples, prior to forming the layer, the method further comprises attaching a silane or a silane derivative to the flow cell surface to form a silanized surface. Also in some of these examples, the layer of the azide functionalized molecule is poly(N-(5-azidoacetamidylpentyl) acrylamide-co-acrylamide).

An example of this further aspect further comprises filtering unreacted copper (I) sulfide mineral from the catalytically active substance prior to reacting the catalytically active substance with the azide functionalized molecule on the flow cell surface.

It is to be understood that any features of this aspect of the method may be combined together in any desirable manner. Moreover, it is to be understood that any combination of features from this method and/or the graft mix and/or the other method and/or from the catalytically active substance may be used together, and/or that any features from any or all of these aspects may be combined with any of the features of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 1 is a flow diagram illustrating an example of a method disclosed herein;

FIGS. 2A, 2B, and 2E are schematic cross-sectional views depicting an example of adding surface chemistry to a patterned substrate using a second example of a graft mix;

FIGS. 3A through 3D are schematic cross-sectional views depicting an example of adding surface chemistry to a non-patterned substrate using a first example of a graft mix, and FIGS. 3A, 3B, and 3D are schematic cross-sectional views depicting an example of adding surface chemistry to a non-patterned substrate using a second example of a graft mix;

DETAILED DESCRIPTION

Figure 2A:
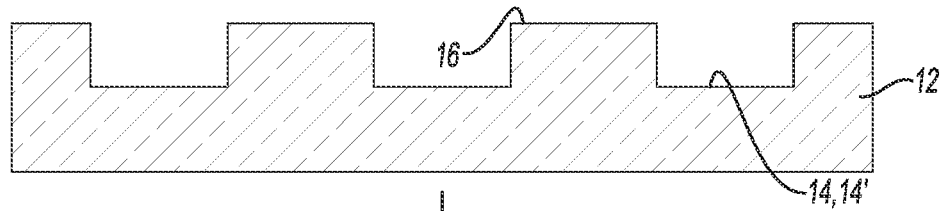
FIGS. 2A through 2E are schematic cross-sectional views depicting an example of adding surface chemistry to a patterned substrate using a first example of a graft mix.

Examples of the method disclosed herein involve the formation of a catalytically active substance that contains copper (Cu) in its +1 oxidation state. Copper (I) sulfide minerals are copper monosulfides, where $1.6 \leq Cu/S \leq 2$. Examples of copper (I) sulfide minerals are chalcocite ($Cu_2S$) or djurleite ($Cu_{31}S_{16}$) or digenite ($Cu_9S_5$). In some aspects, a catalytically active substance is formed using a mineral copper (I) sulfide, which functions as the source of the active copper species ($Cu^+$). In the examples disclosed herein, the copper (I) sulfide mineral is reacted with an alkyne functionalized molecule and an azide functionalized molecule to form a triazole. In some aspects, the copper (I) sulfide reacts with an alkyne functionalized molecule to form the catalytically active substance, which includes the copper (I) sulfide mineral particle and the alkyne functionalized molecule directly bound to the surface of the mineral copper (I) sulfide particle. It has been found that this reaction can be performed without coordinating a $Cu^{2+}$ species to a stabilizing ligand (e.g., to avoid precipitation) and without exposing the stabilized $Cu^{2+}$ species to a reducing agent (e.g., ascorbate) to generate the catalytically active copper species. Avoiding the use of additional reagents for ligand coordination and $Cu^{2+}$ reduction is desirable as these additional reagents can add to the complexity and cost of the reaction, can result in undesirable side reactions, and can involve undesirable or toxic reactants. Without ligand coordination and reduction, the example method disclosed(s) herein is a simplified process that does not involve extra reagents in addition to the mineral copper (I) sulfide and the alkyne functionalized molecule.

Moreover, it has been found that the heterogeneous reaction of the alkyne functionalized molecule on the surface of the copper (I) sulfide mineral occurs in the absence of light (i.e., is not driven by light), which is unlike polymer stabilized $Cu_2S$ quantum dots.

Still further, in some examples of the method disclosed herein, the alkyne functionalized molecule is a primer including an alkyne functional group. In these examples, the catalytically active substance may be used in a copper (I) catalyzed azide-alkyne cycloaddition reaction to couple the alkyne functional group of the primer to an azide functionalized molecule. This cycloaddition reaction can take place in the presence of an aqueous medium and in the presence of oxygen without disproportionating the active copper species to $Cu^0$ and $Cu^{2+}$, in part because the active copper species is coordinated to the primer and to sulfur in the catalytically active substance.

Copper catalyst removal has proven to be difficult in other azide-alkyne cycloaddition reactions, in part because of the tendency of the active copper species disproportionate to $Cu^0$ and $Cu^{2+}$. Removal techniques that are often used include ion-exchange or liquid-liquid extraction techniques. Other techniques to ease copper catalyst removal have included incorporating a fluorous tag to the catalyst, where the fluorous tag facilitates the removal of the tagged catalyst by solid-phase extraction techniques. Unlike these techniques, which involve sophisticated tools and/or additional materials to facilitate copper catalyst removal, some examples of the method disclosed herein involve simple methods, such as centrifugation or filtering, for removing the unreacted mineral copper (I) sulfide. These simple techniques may be used, because, in some examples, a single graft mix (referred to herein as the second example of the graft mix) includes a dissolved azide-alkyne reaction product and undissolved, unreacted copper (I) sulfide mineral, the latter of which can be separated by centrifugation or filtering.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms. An alkyne functionalized molecule is any molecule including an alkyne functional group.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

As used herein, the term "attached" refers to the state of two things being joined, fastened, adhered, connected or bound to each other. For example, a nucleic acid can be attached to a polymer by a covalent or non-covalent bond. A covalent bond is characterized by the sharing of pairs of electrons between atoms. In an example, the covalent bond may be a coordination bond between the copper (I) sulfide and the alkyne functionalized molecule. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —$N_3$. An azide functionalized molecule is any molecule including an azide functional group.

As used herein, the "bonding region" refers to an area on a support or substrate that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated, and results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, inkjet printing, or the like.

As used herein, the term "depression" refers to a discrete concave feature in a patterned substrate having a surface opening that is completely surrounded by interstitial region(s) of the patterned substrate surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As an example, the depression can be a well. Also as used herein, a "functionalized depression" refers to the discrete concave feature where the polymer and primer(s) are attached.

The term "each," when used in reference to a collection of items, is intended to identify an individual item in the collection, but does not necessarily refer to every item in the collection. Exceptions can occur if explicit disclosure or context clearly dictates otherwise.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like, in the chamber.

As used herein, a "flow channel" may be an area defined between two bonded components, which can selectively receive a liquid sample. In some examples, the flow channel may be defined between a patterned substrate and a lid, and thus may be in fluid communication with one or more depressions defined in the patterned substrate. In other examples, the flow channel may be defined between a non-patterned substrate and a lid.

The term "functionalized layer" refers to a layer including the azide functionalized molecule having the alkyne functionalized molecule coupled thereto.

As used herein, the term "graft mix" refers to a mixture or solution including surface chemistry components. A first example of the graft mix disclosed herein includes the copper (I) sulfide and the alkyne functionalized molecule and/or a reaction product of the copper (I) sulfide and the alkyne functionalized molecule (which is referred to herein as the catalytically active substance). This first example of the graft mix may also include a solvent. As described further herein, the first example of the graft mix may be used to introduce the alkyne functionalized molecule to an already formed layer of the azide functionalized molecule. A second example of the graft mix disclosed herein includes the copper (I) sulfide, the alkyne functionalized molecule, and the azide functionalized molecule, and/or the catalytically active substance, and/or a reaction product of the catalytically active substance and the azide functionalized molecule. This second example of the graft mix may also include a solvent. As described further herein, the second example of the graft mix may be used to introduce a functionalized layer to a flow cell substrate.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

As used herein, "hydroxy" or "hydroxyl" refers to an —OH group.

As used herein, the term "interstitial region" refers to an area in a substrate or on a surface that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of the coating layer and primer(s) that exceeds the amount or concentration present at the interstitial regions. In some examples, the coating layer and primer(s) may not be present at the interstitial regions.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The term "flow cell substrate" or "substrate" refers to a support upon which surface chemistry may be added. The term "patterned substrate" refers to a support in which or on which depressions are defined. The term "non-patterned substrate" refers to a substantially planar support. The substrate may be a wafer, a panel, a rectangular sheet, a die, or any other suitable configuration. The substrate is generally rigid and is insoluble in an aqueous liquid. The substrate may be inert to a chemistry that is used to modify the depressions. For example, a substrate can be inert to chemistry used to form the polymer layer, to attach the primer(s) to the polymer layer, etc. Examples of suitable substrates include epoxy siloxane, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The substrate may also be glass or silicon, with a coating layer of tantalum oxide or another ceramic oxide at the surface.

As used herein, "plasma ashing" refers to a process of removing organic matter from a substrate by an oxygen plasma. The products that result from plasma ashing may be removed with a vacuum pump/system. Plasma ashing can activate the substrate by introducing reactive hydroxyl groups.

The "polymer layer" referred to herein is intended to mean a semi-rigid material that is permeable to liquids and gases. The polymer layer may be a hydrogel that can swell when liquid is taken up and that can contract when liquid is removed by drying. In the examples disclosed herein, the polymer layer may include the azide functionalized molecule that can react with an alkyne functional group. In an example, the azide functionalized molecule and the polymer layer is poly(N-(5-azidoacetamidylpentyl) acrylamide-co-acrylamide) (PAZAM).

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the azide functionalized molecule. The primer length can be any number of bases long and can include a variety of non-natural nucleotides. In an example, the sequencing primer is a short strand, ranging from 20 to 40 bases.

As used herein, the terms "silane" and "silane derivative" refer to an organic or inorganic compound containing one or more silicon atoms. An example of an inorganic silane compound is $SiH_4$, or halogenated $SiH_4$ where hydrogen is replaced by one or more halogen atoms. An example of an organic silane compound is $X—R^B—Si(OR^C)_3$, wherein X is a nonhydrolyzable organic group, such as amino, vinyl, methacrylate, epoxy

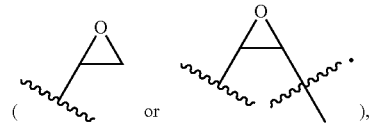

sulfur, alkyl, alkenyl, or alkynyl; $R^B$ is a spacer, for example $—(CH_2)_n—$, wherein n is 0 to 1000; $R^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the terms "silane" and "silane derivative" can include mixtures of different silane and/or silane derivative compounds.

In some examples, the silane or silane derivative includes an unsaturated moiety that is capable of reacting with a functional group of the azide functionalized molecule. As used herein, the term "unsaturated moiety" refers to a chemical group which includes cycloalkenes, cycloalkynes, heterocycloalkenes, heterocycloalkynes, or optionally substituted variants thereof including at least one double bond or one triple bond. The unsaturated moieties can be monovalent or di-valent. When the unsaturated moiety is monovalent, cycloalkene, cycloalkyne, heterocycloalkene, and heterocycloalkyne are used interchangeably with cycloalkenyls, cycloalkynyls, heterocycloalkenyl, and heterocycloalkynyl, respectively. When the unsaturated moiety is di-valent, cycloalkene, cycloalkyne, heterocycloalkene, and heterocycloalkyne are used interchangeably with cycloalkenylene, cycloalkynylene, heterocycloalkenylene, and heterocycloalkynylene, respectively.

The unsaturated moiety can be covalently attached either directly to the silicon atoms of the silane or silane derivative, or indirectly attached via linkers. Examples of suitable linkers include optionally substituted alkylenes (i.e., bivalent saturated aliphatic radicals (such as ethylene) regarded as being derived from an alkene by opening of the double bond or from an alkane by removal of two hydrogen atoms from different carbon atoms), substituted polyethylene glycols, or the like.

A "spacer layer," as used herein refers to a material that bonds two components together. In some examples, the spacer layer can be a radiation-absorbing material that aids in bonding, or can be put into contact with a radiation-absorbing material that aids in bonding.

The term "surface chemistry," as used herein refers to chemically and/or biologically active component(s) that are incorporated into the chamber of the flow cell. Examples of the surface chemistry disclosed herein include the primer, which may be part of the catalytically active substance, and which may be attached to the azide functionalized molecule. As such, one example of the surface chemistry is the functionalized layer.

An example of the method 100 is depicted in FIG. 1. The method 100 includes reacting a copper (I) sulfide mineral with an alkyne functionalized molecule to form a catalytically active substance (as shown at reference numeral 102), and reacting the catalytically active substance with an azide functionalized molecule to couple the catalytically active substance with the azide functionalized molecule (as shown at reference numeral 104).

As previously mentioned, the copper (I) sulfide mineral may be any copper (I) sulfide mineral, such as chalcocite ($Cu_2S$) or djurleite ($Cu_{31}S_{16}$) or digenite ($Cu_9S_5$). The mineral form is the naturally occurring form of the copper (I) sulfide mineral. As such, the copper (I) sulfide mineral is not stabilized with a surface polymer or other stabilizing compound, is not exposed to surface treatments, etc. The copper (I) sulfide mineral may have any suitable particle size. In an example, the copper (I) sulfide mineral has an average particle size less than or equal to 45 μm. In another example, the copper (I) sulfide mineral has an average particle size ranging from about 500 nm to about 45 μm. In still another example, the copper (I) sulfide mineral has an average particle size ranging from about 1 μm to about 40 μm. While several examples have been provided, the average particle size of the copper (I) sulfide mineral may be higher or lower.

Any alkyne functionalized molecule may be used in the examples disclosed herein. In an example, the alkyne functionalized molecule is a primer, such as a sequencing primer, that includes an alkyne functional group. The primer may be any forward amplification primer or reverse amplification primer that includes the alkyne functional group. Specific examples of suitable primers include P5 and/or P7 primers, which are used on the surface of commercial flow cells sold by Illumina Inc. for sequencing on HISEQ™, HISEQX™, MISEQ™, MISEQX™, NEXTSEQ™, NOVASEQ™, GENOME ANALYZER™, and other instrument platforms.

To form the catalytically active substance, the copper (I) sulfide mineral and the alkyne functionalized molecule are combined together and are incubated for a time period, allowing the components to react. The components may be combined in any solvent that the alkyne functionalized molecule is soluble in. In some examples, it may also be desirable to select a solvent that can dissolve the azide functionalized molecule, as the reaction of the catalytically active substance with the azide functionalized molecule may also take place in the solvent. In an example, the solvent is a polar solvent. Examples of suitable polar solvents are selected from the group consisting of water, a sodium carbonate ($NaHCO_3$) buffer, a potassium phosphate ($KH_2PO_4$) buffer, dimethyl sulfoxide (DMSO), dimethylformamide (DMF), acetone, acetonitrile, butanol, propanol, ethanol, methanol, and mixtures thereof. It is believed that other solvents may be used, and in some instances, the catalytically active substance may not be soluble in, or may be partially soluble in these other solvents.

An example of reacting the copper (I) sulfide mineral with the alkyne functionalized molecule includes forming a mixture (i.e., the first example of the graft mix) of the copper (I) sulfide mineral, the alkyne functionalized molecule, and the solvent of the alkyne functionalized molecule, and maintaining the first example of the graft mix at a temperature that is above a freezing point of the solvent and below a boiling point of the solvent for a time up to about 50 days. While the reaction may be initiated instantaneously upon the combination of the copper (I) sulfide mineral and the alkyne functionalized molecule, the incubation period may be prolonged in order to ensure the reaction is complete.

The pH of the first example of the graft mix may range from about 4 to about 12, depending, in part, upon the solvent used and whether the solvent will be present during the subsequent reaction of the catalytically active substance with the azide functionalized molecule. For aqueous solvents, a suitable buffer or strong acid may be used to adjust the pH.

In one example to form the first example of the graft mix, the alkyne functionalized molecule may be added to the solvent to form a solution, and then the copper (I) sulfide mineral may be added to the solution. In another example to form the first example of the graft mix, the alkyne functionalized molecule and the copper (I) sulfide mineral may be added to the solvent. In still another example to form the first example of the graft mix, the solution may be added to the copper (I) sulfide mineral. For example, the copper (I) sulfide mineral may be packed in a column, and the solution of the alkyne functionalized molecule in the solvent may be flowed through the column to generated the catalytically active substance. In any of these examples, a stoichiometric excess of the copper (I) sulfide mineral (with respect to the concentration of the alkyne functionalized molecule in the solution) may be added. The amount of copper (I) sulfide mineral used may also depend, in part, upon the average particle size of the copper (I) sulfide mineral. Smaller copper (I) sulfide mineral particles have a higher surface area to volume ratio than larger copper (I) sulfide mineral particles, and thus smaller amounts of the smaller copper (I) sulfide mineral particles may be used as compared to the amounts of the larger copper (I) sulfide mineral particles that may be used.

The first example of the graft mix may include from about 1 μM to about 100 μM of the alkyne functionalized molecule and from about 0.1 M to about 3 M of the copper (I) sulfide mineral particles. Any concentration of the alkyne functionalized molecule may be used, although the upper limit depends upon the solubility of the alkyne functionalized molecule in the solvent used. As previously described, any concentration of the copper (I) sulfide mineral may be used, as long as it is in stoichiometric excess of the concentration of the alkyne functionalized molecule.

As a specific example of the first example of the graft mix, the P5 and P7 primers (having an alkyne functional group attached thereto) and a stoichiometric excess of $Cu_2S$ particles are mixed into 0.5 M or 1 M sodium carbonate buffer at a pH of about 10. As another specific example of the first example of the graft mix, the P5 and P7 primers (having an alkyne functional group attached thereto) and a stoichiometric excess of $Cu_2S$ particles are mixed into deionized water or dimethyl sulfoxide. As still another specific example of the first example of the graft mix, the P5 and P7 primers (having an alkyne functional group attached thereto) and a stoichiometric excess of $Cu_2S$ particles are mixed into 50 mM potassium phosphate buffer at a pH of about 8.

As such, some examples of first example of the graft mix include the primer including the alkyne functional group, the solvent of the primer, and the copper (I) sulfide mineral. In some examples, the first example of the graft mix includes a stoichiometric excess of the copper (I) sulfide mineral with respect to the primer. In one example, the first example of the graft mix includes from about 1 μM to about 20 μM of the primer, and from about 0.1 M to about 3 M of the copper (I) sulfide mineral. Since the reaction between the alkyne functional group and the copper (I) sulfide mineral may occur substantially instantaneously, the first example of the graft mix may include the catalytically active substance in addition to any unreacted primers (or other alkyne functionalized molecule), any unreacted copper (I) sulfide mineral, and the solvent.

Once the mixture (first example of the graft mix) is prepared, the first example of the graft mix is maintained at a temperature that is above a freezing point of the solvent and below a boiling point of the solvent for an incubation period of up to about 50 days. As such, the temperature at which the mixture is maintained depends, in part, upon the solvent used for the reaction. It has been found that the catalytically active substance formed as a result of the reaction is stable and still catalytically active when incubated for up to about 50 days. It is to be understood, however, that the incubation period may be longer if, at the end of the period, the catalytically active substance remains stable and catalytically active. In some examples, maintaining the first example of the graft mix involves allowing the mixture to sit for the incubation period without any additional heating. In other examples, maintaining the first example of the graft mix involves heating the mixture to the desired temperature. For example, maintaining the first example of the graft mix may involve heating the first example of the graft mix to a temperature ranging from about 30° C. to about 60° C. for a time ranging from about 30 minutes to about 90 minutes.

The reaction to form the catalytically active substance is not driven by light, and thus may be performed in a dark container or oven, or may take place in ambient light. No additional light is used to drive the reaction.

The method may involve mixing the copper (I) sulfide mineral and the alkyne functionalized molecule during the reacting. For example, the first example of the graft mix may be stirred sporadically or continuously while being incubated. As mentioned herein, the method may also involve flowing the solution of the alkyne functionalized molecule through a column of the copper (I) sulfide mineral.

In the first example of the graft mix and during the incubation period, the copper (I) sulfide reacts with the alkyne functional group of the alkyne functionalized molecule to form the catalytically active substance. More particularly, the alkyne of the alkyne functionalized molecule may undergo a heterogeneous reaction on the surface of the copper (I) sulfide. As such, the alkyne may undergo a chemical change at an interface, e.g., on the surface of the solid copper (I) sulfide catalyst. As such, the alkyne functionalized molecule is bound directly to the surface of the solid copper (I) sulfide mineral particle. The resulting substance may be in the form of clusters, which may be soluble in the solvent used in the reaction. in these clusters, the alkyne functionalized molecule may be coordinated to the $Cu^+$ on the surface of the solid copper (I) sulfide. A single cluster includes a single copper (I) sulfide particle with one or more alkyne functionalized molecules coordinated thereto. A single copper (I) sulfide particle has many potential alkyne binding sites, the number of which depends on the size of the particle. The size of the cluster that is formed is defined by the size of the copper (I) sulfide particle (which may be determined, e.g., by dynamic light scattering (DLS)) and the size of the alkyne functionalized molecule that is used. In some examples, the cluster is a nanocluster that has a size ranging from about 1 nm to less than 1000 nm). In other examples, the cluster has a size of about 2 μm or less, and thus may be a microcluster or a nanocluster.

When the substance is formed, the first example of the graft mix is a liquid mixture that may include the solvent, the catalytically active substance (which may be dissolved in the solvent), and any unreacted copper (I) sulfide mineral particles. The first example of the graft mix may then be stored (e.g., up to about 50 days if the incubation period is shorter), used as is in a reaction with the azide functionalized polymer, or subjected to a process that removes unreacted copper (I) sulfide mineral particles prior to being used in a reaction with the azide functionalized polymer. As such, while not shown in FIG. 1, one example of the method 100 may include filtering unreacted copper (I) sulfide mineral from the catalytically active substance in the first example of the graft mix prior to reacting the catalytically active substance with the azide containing molecule.

To remove unreacted copper (I) sulfide mineral particles, the first example of the graft mix may be filtered or sedimented. Filtering may be accomplished using any suitable filter that will remove any unreacted copper (I) sulfide mineral particles from the first example of the graft mix. In an example, a 0.2 μm filter is used. The filter size may depend upon the average particle size of the copper (I) sulfide mineral used in the process. Sedimentation may be accomplished using centrifugation and then removing the liquid from the settled particles. After filtering, or sedimentation, or some other process to separate the unreacted copper (I) sulfide mineral from the remainder of the first example of the graft mix, the first example of the graft mix is a liquid mixture that may include the solvent and the catalytically active substance dissolved or dispersed in the solvent. When the unreacted copper (I) sulfide mineral particles are filtered, the first example of the graft mix may transition from being black to being substantially colorless, or having a slightly transparent blue color.

The stored or non-stored and filtered or unfiltered first example of the graft mix may then be combined with an azide functionalized molecule to react the catalytically active substance with the azide functionalized molecule to couple the catalytically active substance with the azide functionalized molecule.

The azide functionalized molecule may be any molecule (e.g., monomer, polymer, etc.) that includes an azide functional group to react with the alkyne of the catalytically active substance. An example of the azide functionalized molecule includes an acrylamide polymer, such as poly(N-(5-azidoacetamidylpentyl)acrylamide-co-acrylamide, PAZAM. PAZAM, and other forms of acrylamide copolymer, are generally represented by a recurring unit of Formula (I):

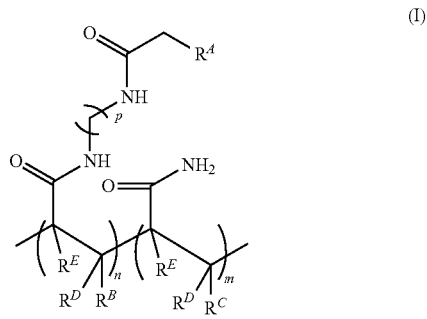

wherein:
  $R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;

$R^B$ is H or optionally substituted alkyl;

$R^C$, $R^D$, and $R^E$ is independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in Formula (I) are representative, and the monomeric subunits may be present in any order in the polymer structure (e.g., random, block, patterned, or a combination thereof).

Specific examples of PAZAM are represented by:

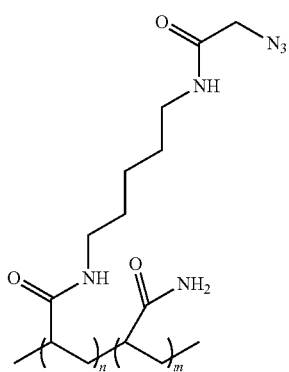

wherein n is an integer in the range of 1-20,000, and m is an integer in the range of 1-100,000. As with Formula (I), one of ordinary skill in the art will recognize that the "n" and "m" subunits are recurring units that are present in random order throughout the polymer structure.

The molecular weight of the Formula (I) or PAZAM polymer may range from about 10 kDa to about 1500 kDa, or may be, in a specific example, about 312 kDa.

In some examples, the Formula (I) or PAZAM polymer is a linear polymer. In some other examples, the Formula (I) or PAZAM polymer is a lightly cross-linked polymer.

In other examples, the azide functionalized molecule may be a variation of the Formula (I). In one example, the acrylamide unit may be replaced with N,N-dimethylacrylamide

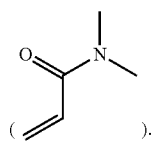

In this example, the acrylamide unit in Formula (I) may be replaced with

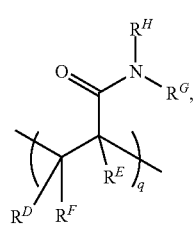

where $R^D$, $R^E$, and $R^F$ are each H, and $R^G$ and $R^H$ are each a methyl group (instead of H as is the case with the acrylamide). In this example, q may be an integer in the range of 1 to 100,000. In another example, the N,N-dimethylacrylamide may be used in addition to the acrylamide unit. In this example, Formula (I) may include

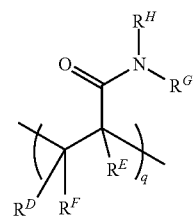

in addition to the recurring "n" and "m" features, where $R^D$, $R^E$, and $R^F$ are each H, and $R^G$ and $R^H$ are each a methyl group. In this example, q may be an integer in the range of 1 to 100,000.

It is to be understood that other azide functionalized molecules may be used, as long as they include the azide functional group to react with the alkyne functionalized molecule, e.g., by interacting with the catalytically active substance. Other examples of suitable azide functionalized molecules include other azidolyzed polyacrylamide polymers or an azidolyzed version of silane free acrylamide (SFA).

The catalytically active substance (from the first example of the graft mix) and the azide functionalized molecule may be mixed together, and the copper (I) sulfide nanoclusters of the substance act as the source of $Cu^+$ for the azide-alkyne cycloaddition reaction between the catalytically active substance and the azide functionalized molecule. The cycloaddition forms azoles to link the azide functionalized molecule to the catalytically active substance. In a more specific example, the cycloaddition forms azoles to link the alkyne group of a primer to the azide group of a polymer. Once the alkyne is bound to an available surface site on the copper (I) sulfide particle, the azide then binds to that surface site as well (via coordination with $Cu^+$), which forms a transition state for the C-N bond forming step. Any 1,2,3-triazole product that forms dissociates from the copper (I) sulfide particle.

The liquid from the first example of the graft mix may be present during the azide-alkyne cycloaddition reaction.

In some examples of the method 100 disclosed herein, the azide-alkyne cycloaddition reaction may take place on a surface of a flow cell. In these examples, the azide functionalized molecule may be a polymer layer on the flow cell substrate, and the first example of the graft mix may be exposed to this polymer layer. In some examples, prior to reacting the catalytically active substance with the azide functionalized molecule, the method 100 further comprises forming a layer of the azide functionalized molecule on a surface of a flow cell (e.g., a flow cell substrate), and the catalytically active substance is reacted with the layer of the azide functionalized molecule on the surface of the flow cell to form a functionalized layer. Examples of these methods will be further described in reference to FIGS. 2A-E and 3A-3D.

In another example of the method 100, a second example of the graft mix is utilized. In this example, the alkyne functionalized molecule may be added to the solvent to form a solution, and the solution may be combined with the azide functionalized molecule. The copper (I) sulfide mineral may then be added to the solution including both the alkyne and the azide functionalized molecules. At the outset, the second example of the graft mix includes the solvent, the alkyne functionalized molecule, the azide functionalized molecule, and the copper (I) sulfide mineral. As the reaction(s) occur, the second example of the graft mix may include the catalytically active substance, the azide functionalized molecule, and any unreacted alkyne functionalized molecule and copper (I) sulfide mineral, or an azide-alkyne reaction product (i.e., the reaction product of the catalytically active substance and the azide functionalized molecule), and any of the other components that have not reacted.

Any of the materials, and or amounts/concentrations set forth for the first example of the graft mix may be used to form the second example of the graft mix.

Once the second example of the graft mix is prepared, the second example of the graft mix is maintained at a temperature that is above a freezing point of the solvent and below a boiling point of the solvent for an incubation period of up to about 50 days. As such, the temperature at which the mixture is maintained depends, in part, upon the solvent used for the reaction. It has been found that the azide-alkyne reaction product formed as a result of the reactions is stable and active when incubated for up to about 50 days. It is to be understood, however, that the incubation period may be longer if, at the end of the period, the azide-alkyne reaction product remains stable and active. In some examples, maintaining the second example of the graft mix involves allowing the mixture to sit for the incubation period without any additional heating. In other examples, maintaining the second example of the graft mix involves heating the mixture to the desired temperature. For example, maintaining the second example of the graft mix may involve heating the second example of the graft mix to a temperature ranging from about 30° C. to about 60° C. for a time ranging from about 30 minutes to about 90 minutes.

To remove unreacted copper (I) sulfide mineral particles, the second example of the graft mix may be filtered or sedimented. Filtering may be accomplished using any suitable filter that will remove any unreacted copper (I) sulfide mineral particles from the second example of the graft mix. In an example, a 0.2 µm filter is used. The filter size may depend upon the average particle size of the copper (I) sulfide mineral used in the process. Sedimentation may be accomplished using centrifugation and then removing the liquid from the settled particles. After filtering, or sedimentation, or some other process to separate the unreacted copper (I) sulfide mineral from the remainder of the second example of the graft mix, the second example of the graft mix is a liquid mixture that may include the solvent and the azide-alkyne reaction product dissolved or dispersed in the solvent.

In some other examples of the method 100 disclosed herein, the second example of the graft mix may be used to form the functionalized layer on the flow cell substrate or support surface. In these examples, the second example of the graft mix may be applied to the flow cell substrate/support surface, and a functional group of the azide-alkyne reaction product can react with functional group(s) on the surface of the flow cell to attach the azide-alkyne reaction product to the surface and form the functionalized layer. Examples of these methods will be further described in reference to FIGS. 2A, 2B and 2E and 3A, 3B, and 3D.

It is to be understood that the surface chemistry (e.g., the functionalized layer) may be added to a surface of a patterned substrate or a non-patterned substrate. The addition of the surface chemistry to the patterned substrate will be described in reference to FIGS. 2A through 2E and the addition of the surface chemistry to the non-patterned substrate will be described in reference to FIGS. 3A through 3D.

FIG. 2A is a cross-sectional view of the patterned substrate 12. The patterned substrate 12 may be a patterned wafer or a patterned die or any other patterned substrate (e.g., panel, rectangular sheet, etc.). Any example of the substrate 12 described herein may be used. The patterned wafer may be used to form several flow cells, and the patterned die may be used to form a single flow cell. In an example, the substrate may have a diameter ranging from about 2 mm to about 300 mm, or a rectangular sheet or panel having its largest dimension up to 10 feet (~3 meters). In an example, the substrate wafer has a diameter ranging from about 200 mm to about 300 mm. In another example, the substrate die has a width ranging from about 0.1 mm to about 10 mm. While example dimensions have been provided, it is to be understood that substrates with any suitable dimensions may be used.

The patterned substrate 12 includes depressions 14 defined on or in an exposed layer or surface of the substrate 12, and interstitial regions 16 separating adjacent depressions 14. In the examples disclosed herein, the depressions 14 become functionalized with surface chemistry (e.g., 20, 22), while the interstitial regions 16 may be used for bonding but will not have primer(s) 22 (shown in FIG. 2E) present thereon.

The depressions 14 may be fabricated in or on the substrate 12 using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the substrate 12.

Many different layouts of the depressions 14 may be envisaged, including regular, repeating, and non-regular patterns. In an example, the depressions 14 are disposed in a hexagonal grid for close packing and improved density. Other layouts may include, for example, rectilinear (i.e., rectangular) layouts, triangular layouts, and so forth. In some examples, the layout or pattern can be an x-y format of depressions 14 that are in rows and columns. In some other examples, the layout or pattern can be a repeating arrangement of depressions 14 and/or interstitial regions 16. In still other examples, the layout or pattern can be a random arrangement of depressions 14 and/or interstitial regions 16. The pattern may include spots, pads, wells, posts, stripes, swirls, lines, triangles, rectangles, circles, arcs, checks, plaids, diagonals, arrows, squares, and/or cross-hatches.

The layout or pattern may be characterized with respect to the density of the depressions 14 (i.e., number of depressions 14) in a defined area. For example, the depressions 14 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per $mm^2$, about 5 million per $mm^2$, about 2 million per $mm^2$, about 1 million per $mm^2$, about 0.1 million per $mm^2$, about 1,000 per $mm^2$, about 100 per $mm^2$, or less. It is to be further understood that the density of depressions 14 on the substrate 12 can be between one of the lower values and one of the upper values selected from the ranges above.

As examples, a high density array may be characterized as having depressions 14 separated by less than about 100 nm, a medium density array may be characterized as having depressions 14 separated by about 400 nm to about 1 μm, and a low density array may be characterized as having depressions 14 separated by greater than about 1 μm. While example densities have been provided, it is to be understood that substrates with any suitable densities may be used.

The layout or pattern may also or alternatively be characterized in terms of the average pitch, i.e., the spacing from the center of the depression 14 to the center of an adjacent interstitial region 16 (center-to-center spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 μm, about 0.5 μm, about 1 μm, about 5 μm, about 10 μm, about 100 μm, or more. Alternatively or additionally, the average pitch can be, for example, at most about 100 μm, about 10 μm, about 5 μm, about 1 μm, about 0.5 μm, about 0.1 μm, or less. The average pitch for a particular pattern of sites 16 can be between one of the lower values and one of the upper values selected from the ranges above. In an example, the depressions 14 have a pitch (center-to-center spacing) of about 1.5 μm. While example average pitch values have been provided, it is to be understood that other average pitch values may be used.

In the example shown in FIGS. 2A through 2E, the depressions 14 are wells 14', and thus the patterned substrate 12 includes an array of wells 14' in a surface thereof. The wells 14' may be micro wells or nanowells. The size of each well 14' may be characterized by its volume, well opening area, depth, and/or diameter.

Each well 14' can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1 \times 10^{-3}$ μm$^3$, about $1 \times 10^{-2}$ μm$^3$, about 0.1 μm$^3$, about 1 μm$^3$, about 10 μm$^3$, about 100 μm$^3$, or more. Alternatively or additionally, the volume can be at most about $1 \times 10^4$ μm$^3$, about $1 \times 10^3$ μm$^3$, about 100 μm$^3$, about 10 μm$^3$, about 1 μm$^3$, about 0.1 μm$^3$, or less. It is to be understood that the functionalized coating layer can fill all or part of the volume of a well 14'. The volume of the coating layer in an individual well 14' can be greater than, less than or between the values specified above.

The area occupied by each well opening on a surface can be selected based upon similar criteria as those set forth above for well volume. For example, the area for each well opening on a surface can be at least about $1 \times 10^{-3}$ μm$^2$, about $1 \times 10^{-2}$ μm$^2$, about 0.1 μm$^2$, about 1 μm$^2$, about 10 μm$^2$, about 100 μm$^2$, or more. Alternatively or additionally, the area can be at most about $1 \times 10^3$ μm$^2$, about 100 μm$^2$, about 10 μm$^2$, about 1 μm$^2$, about 0.1 μm$^2$, about $1 \times 10^{-2}$ μm$^2$, or less. The area occupied by each well opening can be greater than, less than or between the values specified above.

The depth of each well 14' can be at least about 0.1 μm, about 1 μm, about 10 μm, about 100 μm, or more. Alternatively or additionally, the depth can be at most about $1 \times 10^3$ μm, about 100 μm, about 10 μm, about 1 μm, about 0.1 μm, or less. The depth of each well 14' can be greater than, less than or between the values specified above.

In some instances, the diameter of each well 14' can be at least about 50 nm, about 0.1 μm, about 0.5 μm, about 1 μm, about 10 μm, about 100 μm, or more. Alternatively or additionally, the diameter can be at most about $1 \times 10^3$ μm, about 100 μm, about 10 μm, about 1 μm, about 0.5 μm, about 0.1 μm, or less (e.g., about 50 nm). The diameter of each well 14' can be greater than, less than or between the values specified above.

The patterned substrate 12 may be exposed to a series of processes in order to add the surface chemistry 20, 22 in the depression(s) 14.

While not shown, it is to be understood that the patterned substrate 12 may be exposed to a plasma ashing in order to clean and activate the surface. For example, the plasma ashing process may remove organic material and introduce surface hydroxyl or carboxyl groups. Other suitable cleaning processes may be used to clean the substrate 12, depending, in part, on the type of substrate 12. For example, chemical cleaning may be performed with oxidizing agents or caustic solutions. It is to be understood that if the azide functional molecule can attach to the —OH functional groups on the surface, no additional substrate surface preparation may be used.

Figure 2B:
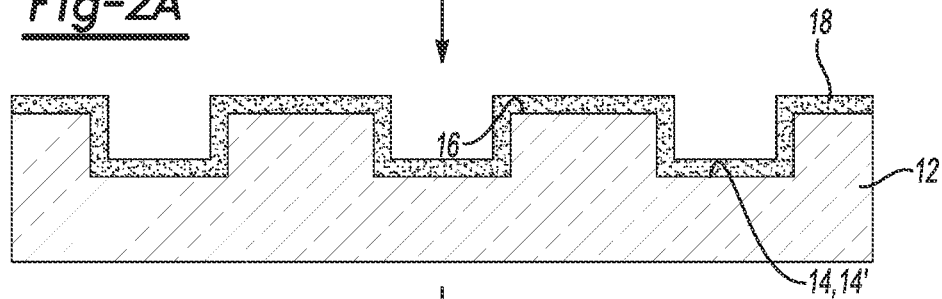
Figure 2C:
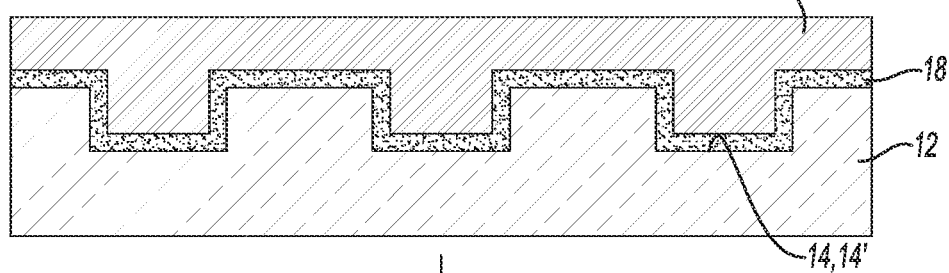
Figure 2D:
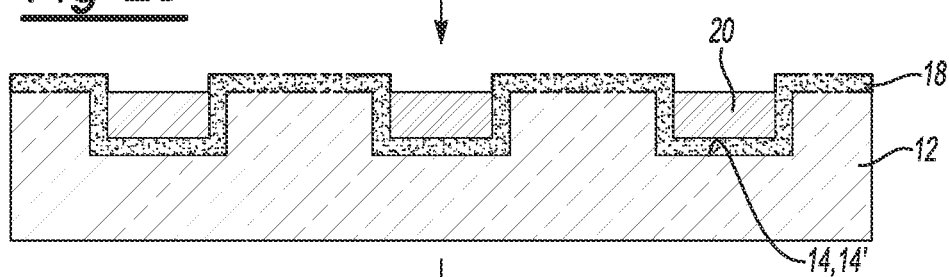
Figure 2E:
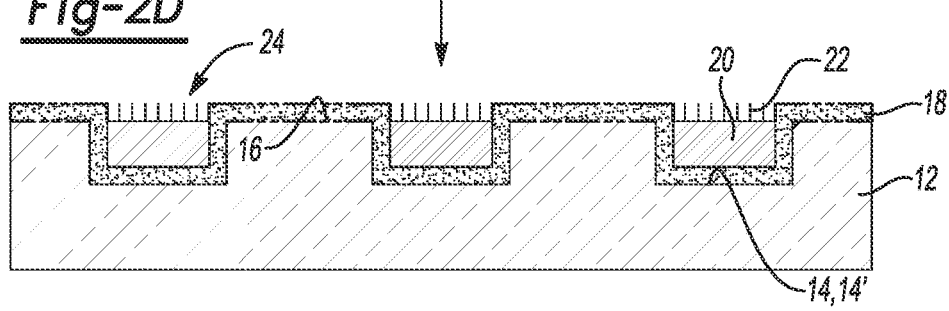

The patterned substrate 12 (shown in FIG. 2A) may then be exposed to a process that will prepare the surface 12 for deposition of the azide functional molecule to form the polymer layer 20 (FIG. 2C) or for the deposition of the second example of the graft mix to form the functionalized layer 24 (FIG. 2E). In an example, the patterned substrate 12 may be exposed to silanization, which attaches a silane or the silane derivative 18 (FIG. 2B) to the patterned substrate 12 surface. Silanization introduces the silane or the silane derivative 18 across the surface, including in the depression 14, 14' (e.g., on the bottom surface and along the side walls) and on the interstitial regions 16.

Silanization may be accomplished using any silane or silane derivative 18. The selection of the silane or silane derivative 18 may depend, in part, upon the azide functionalized molecule that is to be used to form the polymer layer 20 (shown in FIG. 2C) or that is used in the second graft mix, as it may be desirable to form a covalent bond between the silane or silane derivative 18 and the polymer layer 20 or the azide functionalized molecule in the second graft mix. The method used to attach the silane or silane derivative 18 to the substrate 12 may vary depending upon the silane or silane derivative 18 that is being used. Several examples are set forth herein.

In an example, the silane or silane derivative 18 is (3-aminopropyl)triethoxysilane (APTES) or 3-aminopropyl)trimethoxysilane (APTMS) (i.e., X—R$^B$—Si(OR$^C$)$_3$, wherein X is amino, R$^B$ is —(CH$_2$)$_3$—, and R$^C$ is ethyl or methyl). In this example, the substrate 12 surface may be pre-treated with the (3-aminopropyl)triethoxysilane (APTES) or 3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm$^2$ to 30 J/cm$^2$ of energy generates an active nitrene species, which can readily undergo a variety of insertion reactions with PAZAM (e.g., the azide functionalized molecule).

Other silanization methods may also be used. Examples of suitable silanization methods include vapor deposition, the YES method, spin coating, or other deposition methods. Some examples of methods and materials that may be used to silanize the substrate 12 are described herein, although it is to be understood that other methods and materials may be used.

In an example utilizing the YES CVD oven, the patterned substrate 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative 18 (e.g., liquid norbornene silane) may be deposited inside a glass vial and placed inside a glass vacuum desiccator with a patterned substrate 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivative 18, such as those silane or silane derivatives 18 including examples of the unsaturated moieties disclosed herein. As examples, these methods may be used when the silane or silane derivative 18 includes a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo [4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative 18 includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo [6.1.0]non-3-yne). These cycloalkynes can be substituted with any of the R groups described herein.

As shown in FIG. 2B, the attachment of the silane or silane derivative 18 forms a silanized patterned substrate, including silanized depressions and silanized interstitial regions.

In the example shown in FIG. 2C, the silanized patterned substrate may then be exposed to a process that will form the polymer layer 20 on the silanized depressions and silanized interstitial regions.

As described herein, examples of the azide functionalized molecule (used to form the polymer 20) include PAZAM, or any other molecule that is functionalized to interact with the patterned wafer 12 and the subsequently applied primer(s) 22 (as part of the catalytically active complex). The azide functionalized molecule may be present in a solution. In an example, the solution includes PAZAM in an ethanol and water mixture. The polymer layer 20 may be formed on the surface of the silanized patterned wafer (i.e., onto the silanized depressions and the silanized interstitial regions) using any suitable technique. The azide functionalized molecule may be deposited on the surface of the patterned substrate 12 using spin coating, or dipping or dip coating, or flow of the azide functionalized molecule under positive or negative pressure, or other suitable techniques. The resulting layer 20 is shown in FIG. 2C.

The attachment of the polymer layer 20 to the silanized depressions and silanized interstitial regions (i.e., 18) may be through covalent bonding. The covalent linking of the polymer layer 20 to the silanized depressions is helpful for maintaining the polymer layer 20 in the depressions 14, 14' throughout the lifetime of the ultimately formed flow cell during a variety of uses. The following are some examples of reactions that can take place between the silane or silane derivative 18 and the polymer layer 20.

When the silane or silane derivative 18 includes norbornene or a norbornene derivative as the unsaturated moiety, the norbornene or a norbornene derivative can undergo a 1,3-dipolar cycloaddition reaction with an azide/azido group of PAZAM.

When the silane or silane derivative 18 includes cyclooctyne or a cyclooctyne derivative as the unsaturated moiety, the cyclooctyne or cyclooctyne derivative can undergo a strain-promoted azide-alkyne 1,3-cycloaddition (SPAAC) reaction with an azide/azido of PAZAM.

When the silane or silane derivative 18 includes a bicyclononyne as the unsaturated moiety, the bicyclononyne can undergo similar SPAAC alkyne cycloaddition with azides to PAZAM due to the strain in the bicyclic ring system.

While not shown, it is to be understood that in some examples of the method, the patterned substrate 12 may not be exposed to silanization. Rather, the patterned substrate 12 may be exposed to plasma ashing, and then the azide functionalized molecule may be directly spin coated (or otherwise deposited) on the plasma ashed patterned substrate 12 to form the polymer layer 20. In this example, plasma ashing may generate surface-activating agent(s) (e.g., —OH groups) that can adhere the polymer layer 20 to the patterned substrate 12. In these examples, the polymer layer 20 is selected so that it reacts with the surface groups generated by plasma ashing.

After being coated, the azide functionalized molecule may also be exposed to a curing process to form the polymer layer 20 across the entire patterned substrate (i.e., on depression(s) and interstitial region(s)). In an example, curing the azide functionalized molecule may take place at a temperature ranging from room temperature (e.g., about 25° C.) to about 60° C. for a time ranging from about 5 minutes to about 2 hours.

The silanized and coated patterned substrate (shown in FIG. 2C) may be exposed to a cleaning process. This process may utilize a water bath and sonication. The water bath may be maintained at a relatively low temperature ranging from about 22° C. to about 45° C. In another example the water bath temperature ranges from about 25° C. to about 30° C.

The silanized and coated patterned substrate is then exposed to polishing to remove portion(s) of the polymer layer 20 from the silanized interstitial regions. The silanized, coated, and polished patterned substrate is shown in FIG. 2D. The portions of the silane or silane derivative 18 that are adjacent to the interstitial regions 16 may or may not be removed as a result of polishing. As such, in FIGS. 2D and 2E, the portions of the silane or silane derivative 18 that are adjacent to the interstitial regions 16 are shown in phantom, as they may at least partially remain after polishing or they may be removed after polishing. When these silanized portions are completely removed, it is to be understood that the underlying substrate 12 is exposed.

The polishing process may be performed with a gentle chemical slurry (including, e.g., an abrasive, a buffer, a chelating agent, a surfactant, and/or a dispersant) which can remove the thin polymer layer 20, and in some instances, at least part of the silane or silane derivative 18, from the interstitial regions 16 without deleteriously affecting the underlying substrate 12 at those regions. Alternatively, polishing may be performed with a solution that does not include the abrasive particles.

The chemical slurry may be used in a chemical mechanical polishing system to polish the surface of the silanized and coated patterned substrate shown in FIG. 2C. The polishing head(s)/pad(s) or other polishing tool(s) is/are capable of polishing the polymer layer 20 from the interstitial regions 16 while leaving the polymer layer 20 in the depressions 14, 14' and leaving the underlying substrate 12 at least substantially intact. As an example, the polishing head may be a Strasbaugh ViPRR II polishing head.

As mentioned above, polishing may be performed with a polishing pad and a solution without any abrasive. For example, the polish pad may be utilized with a solution free of the abrasive particle (i.e., a solution that does not include abrasive particles).

Polishing removes portion(s) of the polymer layer 20 (and in some instances at least part of the silane or silane derivative 18) from the interstitial regions 16 and leaves portion(s) of the polymer layer 20 in the silanized depressions, as shown in FIG. 2D. Also as mentioned above, the interstitial region(s) 16 may remain silanized after polishing is complete. In other words, the silanized interstitial regions may remain intact after the polishing. Alternatively (as indicated by the phantom portions of 18), the silane or silane derivative 18 may be removed from the interstitial region(s) 16 as a result of polishing.

While not shown, it is to be understood that the silanized, coated, and polished patterned substrate (shown in FIG. 2D) may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

The silanized, coated, and polished patterned substrate shown in FIG. 2D may then be exposed to a grafting process in order to graft the primer 22 to the polymer layer 20 in the depression(s) 14, 14'. In this example, grafting may be accomplished by dunk coating, spray coating, puddle dispensing, or by another suitable method that will attach the primer(s) 22 of the catalytically active substance to the polymer layer 20 in at least some of the depressions 14, 14'. Each of these example techniques utilizes the first example of the graft mix disclosed herein, which includes the catalytically active substance(s). These substances introduce both the primer(s) 22 to be grafted and the $Cu^+$ catalyst for the azide-alkyne cycloaddition reaction.

Dunk coating may involve submerging the patterned substrate (having the polymer layer 20 in the depression(s) 14, 14' thereof) into a series of temperature controlled baths. The baths may also be flow controlled and/or covered with a nitrogen blanket. The baths may include the first example of the graft mix. Throughout the various baths, the primer(s) 22 will attach to the polymer layer 20 in at least some of the depression(s). In an example, the coated and polished patterned substrate will be introduced into a first bath including the first example of the graft mix where an azide-alkyne cycloaddition reaction takes place to attach the primer(s) 22, and then the patterned substrate will be moved to additional baths for washing. The patterned substrate may be moved from bath to bath with a robotic arm or manually. A drying system may also be used in dunk coating.

Spray coating may be accomplished by spraying the first example of the graft mix directly onto the coated and polished patterned substrate. The spray coated substrate may be incubated for up to about 60 minutes at a temperature ranging from about 0° C. to about 70° C. After incubation, the first example of the graft mix may be diluted and removed using, for example, a spin coater.

Puddle dispensing may be performed according to a pool and spin off method, and thus may be accomplished with a spin coater. The first example of the graft mix may be applied (manually or via an automated process) to the coated and polished patterned substrate. The applied first example of the graft mix may be applied to or spread across the entire surface of the coated and polished patterned substrate. The first example of the graft mix coated patterned substrate may be incubated for a time up to about 90 minutes at a temperature ranging from about 0° C. to about 90° C. After incubation, the first example of the graft mix may be diluted and removed using, for example, the spin coater.

The grafting of the primers 22 from the catalytically active substance(s) onto the polymer layer 20 forms the functionalized layer 24, as shown in FIG. 2E.

In another example of the method, the polymer 20 is not applied separately from the primers 22. Rather, the second example of the graft mix, which includes the azide-alkyne reaction product, may be used to form the functionalized layer 24 in a single process.

Referring back to FIG. 2B, the silanized patterned substrate may be exposed to polishing to remove portion(s) of the silane or silane derivative 18 from the silanized interstitial regions. This process leaves the depressions 14, 14' silanized.

The second example of the graft mix may then be applied to the silanized and polished patterned substrate. The application of the second example of the graft mix may be accomplished by dunk coating, spray coating, puddle dispensing, or by another suitable method. Any unreacted azide functional group(s) of the azide-alkyne reaction product react with the silane or silane derivative 18 in at least some of the depressions 14, 14' as previously described in reference to FIG. 2C. In an example, the azide-alkyne reaction product includes PAZAM (e.g., polymer 20) attached to the alkyne of the primer 22, and any unreacted azides of the PAZAM are able to react with the silane or silane derivative 18 in order to attach the azide-alkyne reaction product to the patterned substrate 12. Unlike the first example of the graft mix, which involves multiple steps to form the functionalized layer 24 (described in FIGS. 2C-2E), using the second example of the graft mix enables the functionalized layer 24 (e.g., layer 20 with primers 22 attached) to be formed in a single application (going from FIG. 2B to FIG. 2E).

After being coated, the azide-alkyne reaction product may also be exposed to a curing process to form the functionalized layer 24 in the depression(s) region(s)). In an example, curing the azide-alkyne reaction product may take place at a temperature ranging from room temperature (e.g., about 25° C.) to about 60° C. for a time ranging from about 5 minutes to about 2 hours.

The application of the surface chemistry 20, 22 (i.e., formation of the functionalized layer 24) may be performed so that a bonding region of the patterned substrate 12 remains exposed. The bonding region of the patterned substrate 12 is generally located on some of the interstitial region(s) 16 of the patterned substrate 12 where a lid will be bonded to the patterned substrate 12. When the patterned substrate is a wafer, the bonding region may define the boundaries of several flow cells that are being formed from the wafer. When the patterned substrate is a die, the bonding region may define the outer boundaries of one flow cell that is being formed.

As such, some examples of the method 100 involve bonding a lid to the bonding region of the patterned substrate 12 to form a flow channel that is in selective fluid communication with the depression(s) 14, 14'. When the patterned substrate 12 is a wafer, different areas of the lid may at least partially define respective flow channels that are being formed using the wafer. When the patterned substrate 12 is a die, the lid may define the one or more flow channels that is/are being formed.

The lid may be any material that is transparent to an excitation light that is directed toward the surface chemistry 20, 22 in the depression(s) 14, 14'. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid may be bonded to the bonding region of the patterned substrate 12 using any suitable technique, such as laser bonding, diffusion bonding, anodic bonding, eutectic bonding, plasma activation bonding, glass frit bonding, or others methods known in the art. In an example, a spacer layer may be used to bond the lid to the bonding region of the patterned substrate 12. The spacer layer may be any material that will seal at least some of the interstitial regions 16 (e.g., the bonding region) of the patterned substrate 12 and the lid together.

In one example, the spacer layer may be a radiation-absorbing material that absorbs radiation at a wavelength that is transmitted by the lid and/or the patterned substrate. The absorbed energy, in turn, forms the bond between the spacer layer and the lid and between the spacer layer and the patterned substrate. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer is the radiation-absorbing material, the spacer layer may be positioned at an interface between the lid and the patterned substrate so that the spacer layer contacts the desired bonding region. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer may include a radiation-absorbing material in contact therewith. The radiation-absorbing material may be applied at the interface between the spacer layer and the lid as well as at the interface between the spacer layer and the patterned substrate. As an example, the spacer layer may be polyimide and the separate radiation-absorbing material may be carbon black. In this example, the separate radiation-absorbing material absorbs the laser energy that forms the bonds between the spacer layer and the lid and between the spacer layer and the patterned substrate. In this example, compression may be applied at the respective interfaces while laser energy at a suitable wavelength is applied to the interfaces (i.e., the radiation-absorbing material is irradiated).

When the patterned substrate 12 is a wafer, the spacer layer and sidewalls (of or connected to the lid) may physically separate one flow channel from an adjacent flow channel and may be located at the periphery of the wafers. When the patterned substrate 12 is a die and the flow cell that is being formed is to include a single flow channel or lane, the spacer layer and sidewalls (of or connected to the lid) may be located at the periphery of the die to define the flow channel and seal the flow cell. When the patterned substrate 12 is a die and the flow cell that is being formed is to include multiple isolated flow channels (e.g., eight or four flow channels), the spacer layer and sidewalls (of or connected to the lid) may physically separate one flow channel/lane from an adjacent flow channel/lane and may be located at the periphery of the die. It is to be understood, however, that the spacer layer and sidewalls may be located in any desired region depending on the implementation.

When the patterned substrate 12 is a die, the bonding of the lid forms the flow cell. When the patterned substrate is a wafer, the method 100 may involve additional processing, such as dicing, after the lid is bonded. In one example, the lid may be bonded to the patterned substrate 12 and dicing forms individual flow cells.

As mentioned above, the surface chemistry 20, 22 (functionalized layer 24) may also be added to a non-patterned substrate 12', and these examples will be described in reference to FIGS. 3A through 3D. With a non-patterned substrate 12', a continuous surface would include the same surface chemistry 20, 22 that is found in the wells 14' of FIGS. 2A through 2E. Any of the substrates disclosed herein may be used as the non-patterned substrate 12', except the non-patterned substrate 12' does not include depressions 14 or interstitial regions 16. In this example method, the lid 26 (shown in FIG. 3B) is bonded to the non-patterned substrate 12' at the outset to form the flow channel(s) 30. The lid 26 may be any of the materials and in any of the configurations described herein. The lid 26 may also be bonded to the non-patterned substrate 12' via any of the techniques described herein.

In the example shown in FIG. 3B, the lid 26 includes a top portion 27 integrally formed with sidewall(s) 29. The sidewall(s) 29 are bonded to a bonding region of the non-patterned substrate 12' through the spacer layer 28. The bonding region may be at a periphery of the non-patterned substrate 12', or at any areas where it is desirable to form a boundary of a flow channel 30. In other examples, the spacer layer 28 may form the sidewall(s) and may be attached to an at least substantially planar lid 26.

Together, the lid 26 (including the sidewall(s) 29) and the non-patterned substrate 12' define the flow channel 30. The flow channel 30 may serve to, for example, selectively introduce fluids in order to form the surface chemistry 20, 22 and to selectively introduce reaction components or reactants to the surface chemistry 20, 22 in order initiate designated reactions within the flow channel 30.

Prior to forming the polymer layer 20 (shown in FIG. 3C), the method may involve exposing the non-patterned substrate 12' (via a flow through process) to a cleaning process and/or to another process (e.g., silanization) that prepares the exposed surface of the non-patterned substrate 12' for the subsequent deposition of the azide functionalized molecule (to form the layer 20) or the second example of the graft mix (to form the functionalized layer 24).

Silanization of the non-patterned substrate 12' is shown in FIG. 3B. In this example, silanization attaches the silane or the silane derivative 18 to the exposed portions of the non-patterned wafer surface 12' that are present in the flow channel 30.

Silanization may be accomplished using any silane or silane derivative 18. The selection of the silane or silane derivative 18 may include a functional group that can form a covalent bond with the azide of the azide functionalized molecule (used to form the polymer layer 20 shown in FIG. 3C), or with the azide of the azide-alkyne reaction product in the second example of the graft mix (used to form the functionalized layer 24 shown in FIG. 3D). The method used to attach the silane or silane derivative 18 to the substrate 12' may be a flow through process.

As shown in FIG. 3C, in this example, the polymer layer 20 is then formed on the silane or silane derivative 18, or on other chemistry that has been deposited to prepare the exposed surface of the non-patterned substrate 12' within the flow channel 30.

Any of the azide functionalized molecules described herein may be used. In this example, polymer layer formation may be accomplished by a flow through process. In the flow through process, the azide functionalized molecule may be introduced into the flow channel(s) 30 through respective input port(s) and may be cured. The polymer layer 20 will form on the exposed surface of the non-patterned substrate 12' and polishing does not take place.

As shown in FIG. 3D, the primer 22 is grafted to the polymer layer 20 in the flow channel 30 using the first example of the graft mix that includes the catalytically active substance(s). In this example, grafting may be accomplished by a flow through process. In the flow through process, the first example of the graft mix described herein may be introduced into the flow channel(s) 30 through respective input port(s), may be maintained in the flow channel(s) for a time sufficient (i.e., an incubation period) for the copper (I) catalyzed azide-alkyne cycloaddition reaction to take place, which attaches the primer 22 to the polymer layer 20 to form the functionalized layer 24. The first example of the graft mix may then be removed from respective output port(s). After primer attachment, the additional fluid(s) may be directed through the flow channel(s) to wash the now functionalized flow channel(s) 30. The resulting flow cell 10 in this example is shown in FIG. 3D.

In another example of the method, the polymer 20 is not applied separately from the primers 22. Rather, the second example of the graft mix, which includes the azide-alkyne reaction product, may be used to form the functionalized layer 24 in a single process.

In this example, the second example of the graft mix may then be applied to the silanized non-patterned substrate shown in FIG. 3B. The application of the second example of the graft mix may be accomplished by a flow through process. Any unreacted azide functional group(s) of the azide-alkyne reaction product react with the silane or silane derivative 18 as previously described in herein. In an example, the azide-alkyne reaction product includes PAZAM (e.g., polymer 20) attached to the alkyne of the primer 22, and any unreacted azides of the PAZAM are able to react with the silane or silane derivative 18 in order to attach the azide-alkyne reaction product to the non-patterned substrate 12. Unlike the first example of the graft mix, which involves multiple steps to form the functionalized layer 24 (described in FIGS. 3C-3D), using the second example of the graft mix enables the functionalized layer 24 (e.g., layer 20 with primers 22 attached) to be formed in a single application (going from FIG. 3B to FIG. 3D). Curing of the functionalized layer 24 may also be performed.

While not shown, it is to be understood that the patterned substrate 12 or non-patterned substrate 12' may include inlet and outlet ports that are to fluidically engage other ports (not shown) for directing fluid(s) into the respective flow channels (e.g., from a reagent cartridge or other fluid storage system) and out of the flow channel (e.g., to a waste removal system).

Also while not shown, it is to be understood that some examples of the flow cell may be affixed directly to, and thus be in physical contact with, a detection device (not shown) through one or more securing mechanisms (e.g., adhesive, bond, fasteners, and the like). The detection device may include a CMOS device (which includes a plurality of stacked layers including, for example, silicon layer(s), dielectric layer(s), metal-dielectric layer(s), metal layer(s), etc.) and optical components. The optical components may be arranged such that an optical sensor of the detection device is at least substantially aligned with, and thus is operatively associated with, a single optical waveguide of the detection device and the surface chemistry 20, 22 within a single depression 14, 14' or within a flow channel 30 of the flow cell.

Also while not shown, it is to be understood that instead of being bonded to a lid 26, a functionalized substrate (with surface chemistry, 20, 22 thereon or in depression(s) 14 thereof) may be bonded to another functionalized substrate with surface chemistry, 20, 22 thereon on in depression(s) thereof. The two functionalized surfaces can face each other and can have a flow channel defined therebetween. A spacer layer and suitable bonding method may be used to bond two of the functionalized substrates together.

The flow cells disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques and in examples using a patterned substrate, since the functional polymer layer 20 and attached sequencing primer(s) 22 are present in the functionalized depressions (i.e., 14, 14' with surface chemistry 20, 22 thereon) and not on the interstitial regions 16, amplification will be confined to the functionalized depressions. In other examples, amplification can take place across an entire flow cell channel (e.g., channel 30).

As one example, a sequencing by synthesis (SBS) reaction may be run on a system such as the HISEQ™, HISEQX™, MISEQ™, NOVASEQ™, or NEXTSEQ™ sequencer systems from Illumina (San Diego, CA). In SBS, extension of a nucleic acid primer along a nucleic acid template is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the primer 22 (thereby extending the primer 22) in a template dependent fashion such that detection of the order and type of nucleotides added to the primer 22 can be used to determine the sequence of the template. For example, to initiate a first SBS cycle, one or more labeled nucleotides, DNA polymerase, etc., may be delivered into/through the flow channel 30, etc. that houses an array of primers 22. The functionalized depressions (i.e., 14, 14' with surface chemistry 20, 22 thereon), where primer extension causes a labeled nucleotide to be incorporated, can be detected through an imaging event. During an imaging event, an illumination system (not shown) may provide an excitation light to the functionalized depressions (i.e., 14, 14' with surface chemistry 20, 22 thereon).

In some examples, the nucleotides can further include a reversible termination property that terminates further primer extension once a nucleotide has been added to the primer 22. For example, a nucleotide analog having a reversible terminator moiety can be added to the primer 22 such that subsequent extension cannot occur until a deblocking agent is delivered to remove the moiety. Thus, for examples that use reversible termination, a deblocking reagent can be delivered to the flow channel 30, etc. (before or after detection occurs).

Wash(es) may take place between the various fluid delivery steps. The SBS cycle can then be repeated n times to extend the primer 22 by n nucleotides, thereby detecting a sequence of length n.

While SBS has been described in detail, it is to be understood that the flow cells described herein may be utilized with other sequencing protocol, for genotyping, or in other chemical and/or biological applications.

To further illustrate the present disclosure, examples are given herein. It is to be understood that these examples are provided for illustrative purposes and are not to be construed as limiting the scope of the disclosure.

NON-LIMITING WORKING EXAMPLES

Example 1

A mixture of 0.25 M $Cu_2S$ particles and 10 uM alkyne-P5 and alkyne-P7 primers was prepared in a 0.5 M sodium carbonate buffer at pH 10. This mixture was allowed to incubate at a temperature of 60° C. for a time of about 1 hour. Without filtering, 10 μM of the graft mix (referred to as E1, and an example of the first example of the graft mix disclosed herein) was exposed to a patterned substrate lane/channel including PAZAM in the wells of the patterned substrate.

Three comparative graft mixes were prepared. As two comparative examples, graft mixes of alkyne-P5 and alkyne-P7 primers, $CuSO_4$ (as a catalyst), and N,N,N',N",N"-Pentamethyldiethylenetriamine, with ascorbate (CE1) or without ascorbate (CE2), were prepared. As a third comparative example (CE3), a graft mix of alkyne-P5 and alkyne-P7 primers was prepared. In each of these comparative graft mixes, the solvent was a 0.5 M sodium carbonate buffer. 10 μM of each the comparative graft mixes was exposed to a respective patterned substrate lanes/channels including PAZAM in the wells of the patterned substrate.

A CFR assay was performed to compare the grafting of the primers using the graft mix with the catalytically active substances disclosed herein (E1) and the comparative graft mixes (CE1, CE2, CE3). During a CFR assay, primer grafted surfaces are exposed to fluorescently tagged (Cal Fluor Red) complementary oligos in a buffer solution. These oligos bind to surface bound primers and excess CFR is washed off. The surface is then scanned in a fluorescent detector to measure CFR intensity on the surface to provide a quantitative measure of primers' concentration and health on the surface. After measurement, the oligos are removed with a mild base solution and surfaces are rescanned to confirm all CFR was removed.

Figure 4:
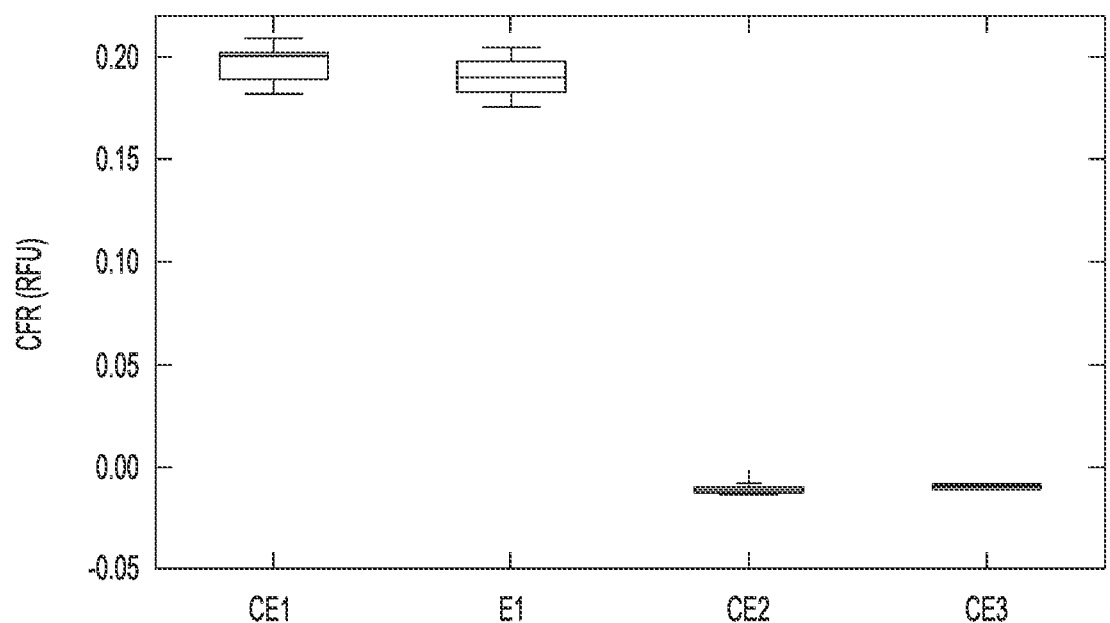
FIG. 4 is a plot of the fluorescence intensity (relative intensity units, RFU) after a surface primer accessibility test (CFR assay) for an example flow cell and comparative flow cells.

The intensity results, in terms of relative intensity units, for the example flow cell and the comparative flow cells are shown in FIG. 4. The relative intensities ranged from about 0.182 to 0.209 for CE1 and ranged from about 0.175 to 0.205 for the example, $Cu_2S$, graft mix (E1). As depicted, the example graft mix E1 including the catalytically active substances was as effective in primer grafting as the comparative graft mix CE1, which included the copper catalyst, the stabilizing ligand, and the ascorbate. The example graft mix E1 also was much more effective in grafting the primers than comparative examples CE2 and CE3.

The example flow cell E1 and the comparative example flow cell CE1 were used for sequencing the PhiX genome, and were tested for the percentage of clusters passing filter (%), quality score (Q30), the intensity after one sequencing cycle, the percentage aligned, and the error rate (%). %Passing filter (PF) is the metric used to describe clusters which pass a chastity threshold and are used for further processing and analysis of sequencing data. Higher %passing filter results in increased yield of non-empty wells of suitable quality for sequencing data. The Q30, percentage aligned and the error rate are quality metrics. More particularly, Q30 is equivalent to the probability of an incorrect base call 1 in 1000 times. This means that the base call accuracy (i.e., the probability of a correct base call) is 99.9%. A lower base call accuracy of 99% (Q20) will have an incorrect base call probability of 1 in 100, meaning that every 100 base pair sequencing read will likely contain an error. When sequencing quality reaches Q30, virtually all of the reads will be perfect, having zero errors and ambiguities. The results are shown in Table 1.

TABLE 1

| Sample | Clusters PF (%) | % >= Q30 | Aligned (%) | Error Rate (%) | Intensity Cycle 1 |
| --- | --- | --- | --- | --- | --- |
| Example | 54.34 +/- 1.3 | 96.12 | 97.92 +/- 0.11 | 0.16 +/- 0.01 | 111 +/- 6 |
| CE1 | 50.77 +/- 1.84 | 94.51 | 95.02 +/- 5.24 | 0.45 +/- 0.44 | 117 +/- 8 |

These results indicate that the primers grafted using the first example of the graft mix (E1) with the catalytically active substance perform as well or better for sequencing.

The results in this example are averages over four image tiles of the lanes/channels that were grafted and tested.

Example 2

Mixtures of 0.25 M $Cu_2S$ particles and 10 uM alkyne-P5 and alkyne-P7 primers were prepared in a 0.5 M sodium carbonate buffer at pH 10. Three mixtures were prepared and allowed to incubate at a temperature of 60° C. for different time periods, including 15 minutes, 30 minutes, and 60 minutes. After filtering, 10 μM of each of the graft mixes (which are examples of the first example of the graft mix disclosed herein) was exposed to a patterned substrate lane/channel including PAZAM in the wells of the patterned substrate.

Figure 5:
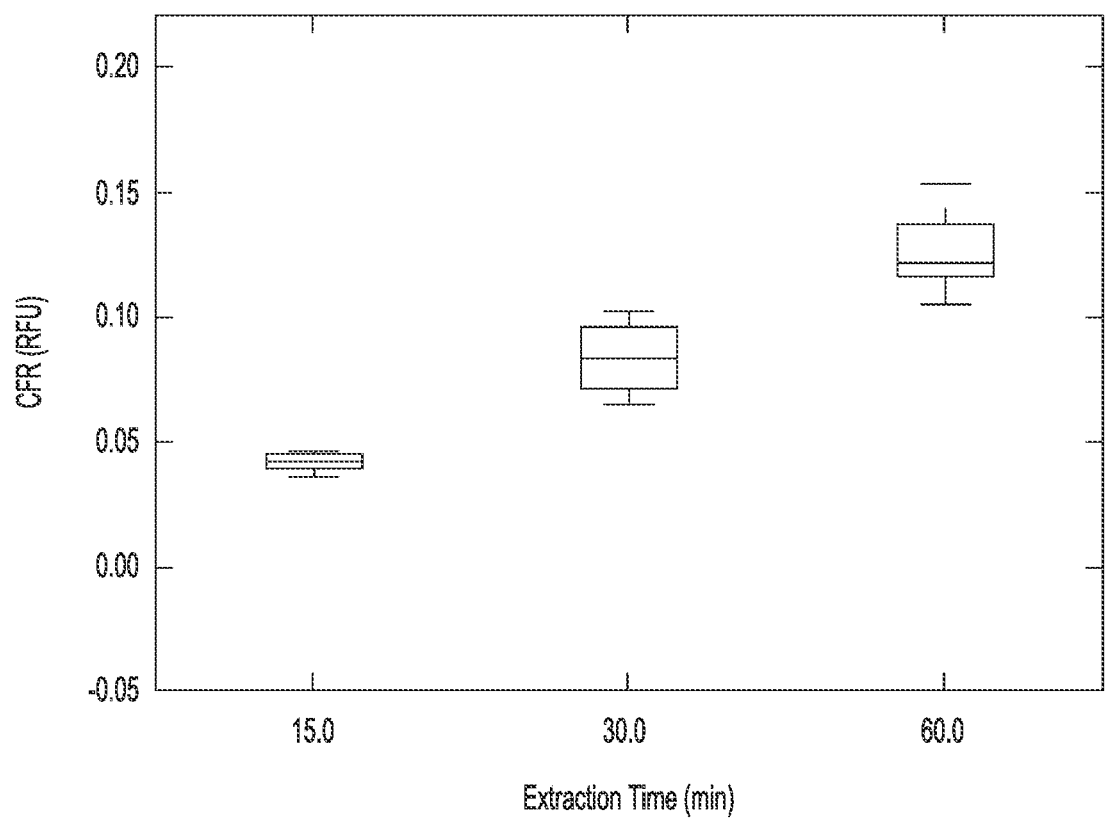
FIG. 5 is a plot of the fluorescence intensity (relative intensity units, RFU) after a surface primer accessibility test (CFR assay) for different example flow cells formed from catalytically active substances that were incubated for different time periods.

The intensity results, in terms of relative intensity units, versus the incubation (or extraction) time for the example flow cells are shown in FIG. 5. The relative fluorescence intensities for these examples ranged from about 0.036 to about 0.152. As depicted, the effectiveness in primer grafting was increased with increasing incubation periods. This indicates that more catalytically active substances were formed when the mixtures were allowed to incubate longer.

Example 3

Different mixtures were prepared to illustrate that the examples disclosed herein generate the catalytically active substances. A comparative mixture 1 included copper (I) sulfide in water, which was not filtered before testing.

Another comparative mixture 2 included copper (I) sulfide in water, which was then filtered before testing. The example included $Cu_2S$ particles and alkyne-P5 and alkyne-P7 primers in water. Each mixture was allowed to incubate at a temperature of 60° C. for a time of about 1 hour, which was filtered before testing.

Figure 6A:
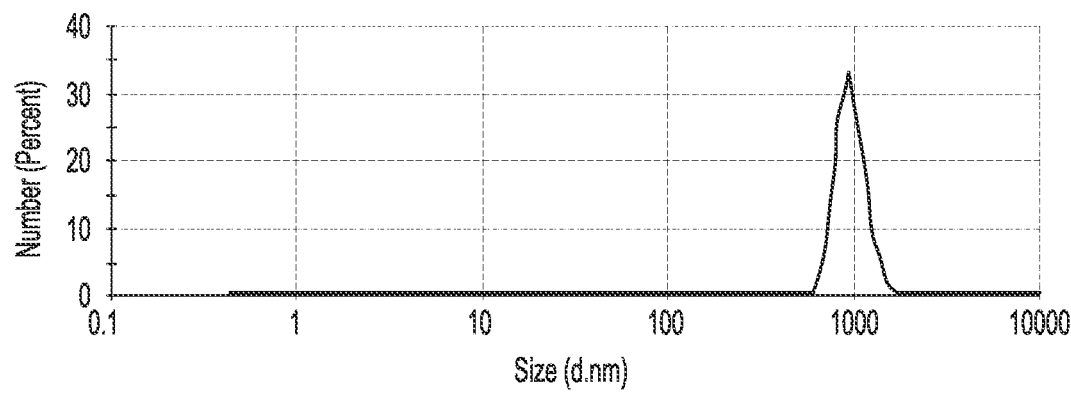
FIGS. 6A through 6C are graphs depicting dynamic light scattering results for different mixtures, the results of which illustrate that the graft mix disclosed herein forms catalytically active substances.
Figure 6B:
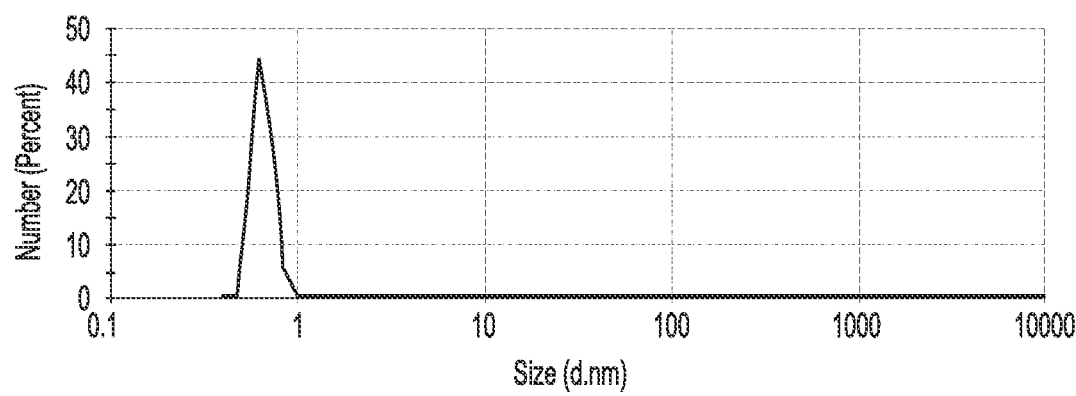
Figure 6C:
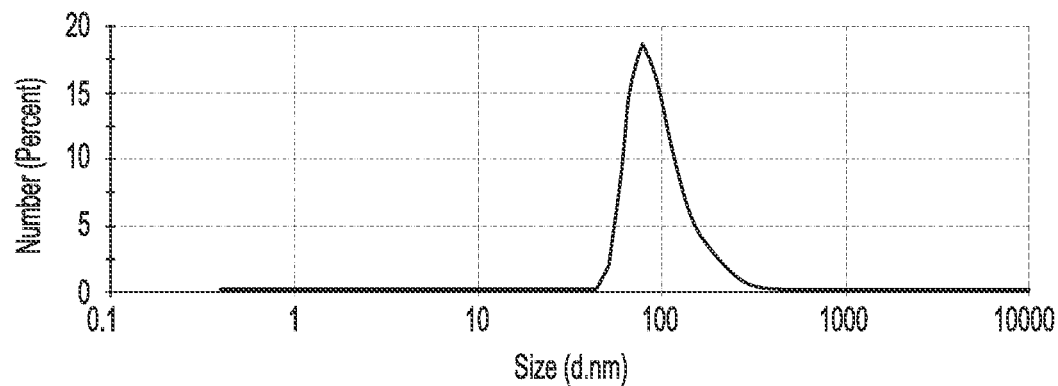

Dynamic light scattering was performed on each of the mixtures. The results are shown in FIGS. 6A (comparative mixture 1), 6B (comparative mixture 2), and 6C (example mixture). The results in FIG. 6A indicate that micron sized copper (I) sulfide particles are present, and the results in FIG. 6B indicate that the micron sized copper (I) sulfide particles were removed during filtering. The results in FIG. 6C indicate that the catalytically active substances were present after filtering was performed.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 500 nm to about 45 µm, should be interpreted to include not only the explicitly recited limits of from about 500 nm to about 45 µm, but also to include individual values, such as about 708 nm, about 945 nm, about 35 µm, etc., and sub-ranges, such as from about 825 mm to about 29 µm, from about 950 nm to about 40 µm, etc. Furthermore, when "about" and/or "substantially" are/is utilized to describe a value, they are meant to encompass minor variations (up to +/− 10%) from the stated value.

While several examples have been described in detail, it is to be understood that the disclosed examples may be modified. Therefore, the foregoing description is to be considered non-limiting.

What is claimed is:

1. A method of making a triazole, comprising:
   forming a catalytically active substance by reacting, in a mixture, i) a copper (I) sulfide mineral selected from the group consisting of chalcocite, djurleite, and digenite, each in its naturally occurring form not stabilized with a surface polymer or other stabilizing compound and having an average particle size ranging from about 500 nm to about 45 µm with ii) an alkyne functionalized molecule, under conditions allowing direct binding of the alkyne functionalized molecule to a surface of the copper (I) sulfide mineral by a coordinate bond, thereby forming the catalytically active substance; and
   reacting the catalytically active substance with an azide functionalized molecule; wherein a concentration of the copper (I) sulfide mineral in the mixture is in stoichiometric excess with respect to the alkyne functionalized molecule.

2. The method as defined in claim 1, wherein the reacting of the copper (I) sulfide mineral with the alkyne functionalized molecule involves:
   forming the mixture of the copper (I) sulfide mineral, the alkyne functionalized molecule, and a solvent of the alkyne functionalized molecule; and
   maintaining the mixture at a temperature that is above a freezing point of the solvent and below a boiling point of the solvent for a time up to about 50 days.

3. The method as defined in claim 2, wherein:
   the solvent is selected from the group consisting of water, a sodium carbonate buffer, a potassium phosphate buffer, and dimethyl sulfoxide; and
   a pH of the mixture ranges from about 4 to about 12.

4. The method as defined in claim 2, wherein the maintaining involves heating the mixture to a temperature ranging from about 30° C. to about 60° C. for a time ranging from about 30 minutes to about 90 minutes.

5. The method as defined in claim 1, wherein prior to reacting the catalytically active substance with the azide functionalized molecule, the method further comprises forming a layer of the azide functionalized molecule on a surface of a flow cell substrate, and wherein the catalytically active substance is reacted with the layer of the azide functionalized molecule on the surface of the flow cell substrate.

6. The method as defined in claim 5, wherein the catalytically active substance is present in a liquid mixture, and wherein the liquid mixture is flowed over the layer of the azide functionalized molecule on the surface of the flow cell substrate.

7. The method as defined in claim 5, wherein prior to forming the layer, the method further comprises attaching a silane or a silane derivative to the surface of the substrate to form a silanized surface.

8. The method as defined in claim 5, further comprising filtering unreacted copper (I) sulfide mineral from the catalytically active substance prior to reacting the catalytically active substance with the azide functionalized molecule.

9. The method as defined in claim 1, wherein the method is performed without ligand coordination and without exposure to a reducing agent.

10. A method of grafting a primer to a flow cell surface, comprising:
    forming a catalytically active substance by reacting, in a mixture, i) a copper (I) sulfide mineral selected from the group consisting of chalcocite, djurleite, and digenite, each in its naturally occurring form not stabilized with a surface polymer or other stabilizing compound and having an average particle size ranging from about 500 nm to about 45 µm with ii) an alkyne functionalized primer, under conditions allowing direct binding of the alkyne functionalized primer to a surface of the copper (I) sulfide mineral by a coordinate bond, thereby forming the catalytically active substance; and
    reacting the catalytically active substance with an azide functionalized molecule on the flow cell surface, thereby grafting the primer to the flow cell surface;
    wherein a concentration of the copper (I) sulfide mineral in the mixture is in stoichiometric excess with respect to the alkyne functionalized molecule.

11. The method as defined in claim 10, wherein the reacting of the copper (I) sulfide mineral with the alkyne functionalized primer involves:
- forming the mixture of the copper (I) sulfide mineral, the alkyne functionalized primer, and a solvent of the alkyne functionalized primer; and
- maintaining the mixture at a temperature that is above a freezing point of the solvent and below a boiling point of the solvent for a time up to about 50 days.

12. The method as defined in claim 11, wherein:
- the solvent is selected from the group consisting of water, a sodium carbonate buffer, a potassium phosphate buffer, and dimethyl sulfoxide; and
- a pH of the mixture ranges from about 4 to about 12.

13. The method as defined in claim 11, wherein the maintaining involves heating the mixture to a temperature ranging from about 30° C. to about 60° C. for a time ranging from about 30 minutes to about 90 minutes.

14. The method as defined in claim 10, wherein prior to reacting the catalytically active substance with the azide functionalized molecule on the flow cell surface, the method further comprises forming a layer of the azide functionalized molecule on the flow cell surface, and wherein the catalytically active substance is reacted with the layer of the azide functionalized molecule on the flow cell surface.

15. The method as defined in claim 14, wherein the catalytically active substance is present in a liquid mixture, and wherein the liquid mixture is flowed over the layer of the azide functionalized molecule on the flow cell surface.

16. The method as defined in claim 14, wherein prior to forming the layer, the method further comprises attaching a silane or a silane derivative to the flow cell surface to form a silanized surface.

17. The method as defined in claim 14, wherein the layer of the azide functionalized molecule is poly (N-(5-azidoacetamidylpentyl) acrylamide-co-acrylamide).

18. The method as defined in claim 10, further comprising filtering unreacted copper (I) sulfide mineral from the catalytically active substance prior to reacting the catalytically active substance with the azide functionalized molecule on the flow cell surface.

19. The method as defined in claim 3, wherein the solvent is the sodium carbonate buffer.

20. The method as defined in claim 12, wherein the solvent is the sodium carbonate buffer.

21. The method as defined in claim 1, wherein the reacting of the alkyne functionalized molecule with the azide functionalized molecule is performed in the absence of light.

22. The method as defined in claim 10, wherein the reacting of the catalytically active substance with the azide functionalized molecule on the flow cell surface is performed in the absence of light.

* * * * *

UNITED STATES PATENT AND TRADEMARK OFFICE
CERTIFICATE OF CORRECTION

PATENT NO. : 12,251,685 B2
APPLICATION NO. : 17/359198
DATED : March 18, 2025
INVENTOR(S) : Kraft It is certified that error appears in the above-identified patent and that said Letters Patent is hereby corrected as shown below:

In the Claims

Column 32, Line 42:
In Claim 8, delete "claim 5," and insert -- claim 1, --.

Signed and Sealed this
Fifteenth Day of July, 2025

Coke Morgan Stewart
*Acting Director of the United States Patent and Trademark Office*